(12) United States Patent
Iftikhar et al.

(10) Patent No.: US 10,856,773 B2
(45) Date of Patent: *Dec. 8, 2020

(54) HAIR DIAMETER MEASUREMENT

(71) Applicant: Conopco, Inc., Englewood Cliffs, NJ (US)

(72) Inventors: Abid Iftikhar, Liverpool (GB); Georgina Elizabeth Lang, Colchester (GB); Robert McKeown, Flintshire (GB); Justin Nobuyuki Minow Pinkney, Cambridge (GB); Stephen Lee Wire, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 129 days.

This patent is subject to a terminal disclaimer.

(21) Appl. No.: 15/767,720

(22) PCT Filed: Oct. 19, 2016

(86) PCT No.: PCT/EP2016/075138
§ 371 (c)(1),
(2) Date: Apr. 12, 2018

(87) PCT Pub. No.: WO2017/072009
PCT Pub. Date: May 4, 2017

(65) Prior Publication Data
US 2018/0296129 A1    Oct. 18, 2018

(30) Foreign Application Priority Data
Oct. 30, 2015 (EP) .................................. 15192432

(51) Int. Cl.
*A61B 5/107* (2006.01)
*G06K 9/32* (2006.01)
(Continued)

(52) U.S. Cl.
CPC .......... *A61B 5/1072* (2013.01); *G01J 3/0264* (2013.01); *G06K 9/32* (2013.01); *G06K 9/3216* (2013.01);
(Continued)

(58) Field of Classification Search
CPC .... G06K 9/4604; G06K 9/32; G06K 9/00885; G06K 2009/3225; G06K 9/3241; G06K 9/3216
See application file for complete search history.

(56) References Cited

U.S. PATENT DOCUMENTS

| 5,164,793 A | 11/1992 | Wolfersberger |
| 5,237,520 A | 8/1993 | White |

(Continued)

FOREIGN PATENT DOCUMENTS

| CN | 1359006 | 7/2002 |
| CN | 1523323 | 8/2004 |

(Continued)

OTHER PUBLICATIONS

Anonymous, Alogorithm—Measuring the average thickness of traces in an image—Stack Overflow, Stackoverflow, Sep. 17, 2010, pp. 1-7; XP055264558, http://stackoverflow.com/questions/3735748/measuring-the-average-thickness-of-traces-in-an-image.

(Continued)

*Primary Examiner* — Ming Y Hon
(74) *Attorney, Agent, or Firm* — Foley & Lardner LLP

(57) ABSTRACT

A method of measuring indications of hair type of a user, the method comprising the steps of: providing a mobile device; providing a reference card, the reference card including one or more reference markers; providing one or more of the user's hairs at the surface of the reference card; acquiring one or more images of said one or more hairs using the mobile device; identifying the path of each of the one or (Continued)

more hairs along the reference card; and calculating the diameter of each hair from the acquired image.

20 Claims, 24 Drawing Sheets

(51) Int. Cl.
*G06K 9/46* (2006.01)
*G01J 3/02* (2006.01)
*A45D 44/00* (2006.01)

(52) U.S. Cl.
CPC ............ *G06K 9/46* (2013.01); *G06K 9/4604* (2013.01); *A45D 2044/007* (2013.01); *G06K 2009/3225* (2013.01)

(56) References Cited

U.S. PATENT DOCUMENTS

| | | | |
|---|---|---|---|
| 5,689,446 | A | 11/1997 | Sundman |
| 6,546,356 | B1 | 4/2003 | Genest |
| 7,051,452 | B2 | 5/2006 | Brooks |
| 10,043,068 | B1 | 8/2018 | Hansen |
| 2004/0168329 | A1 | 9/2004 | Ishimaru |
| 2005/0097762 | A1 | 5/2005 | Biesbrouck |
| 2005/0211599 | A1* | 9/2005 | De La Mettrie ..... A45D 44/005 206/581 |
| 2008/0008368 | A1* | 1/2008 | Matsumoto ............. G06T 19/00 382/128 |
| 2008/0059313 | A1* | 3/2008 | Oblong .................... A61K 8/42 705/14.26 |
| 2009/0220445 | A1* | 9/2009 | Iwata ....................... A61K 8/42 424/70.1 |
| 2010/0014750 | A1* | 1/2010 | Seko .................... G06K 9/3216 382/154 |
| 2010/0026717 | A1* | 2/2010 | Sato ..................... A45D 44/005 345/642 |
| 2010/0106679 | A1* | 4/2010 | Yamaguchi .......... A61B 5/1072 706/54 |
| 2010/0194863 | A1* | 8/2010 | Lopes ...................... G06T 7/12 348/50 |
| 2012/0046873 | A1* | 2/2012 | Rabin .................. A61N 5/0617 702/19 |
| 2012/0189181 | A1* | 7/2012 | Hirano .................. G06T 7/0012 382/128 |
| 2012/0320191 | A1 | 12/2012 | Meschkat et al. |
| 2013/0044193 | A1* | 2/2013 | Kulkarni ............ G06K 9/00671 348/51 |
| 2013/0249902 | A1* | 9/2013 | Byrne .................. G06T 15/503 345/419 |
| 2014/0118521 | A1 | 5/2014 | Conti et al. |
| 2014/0193039 | A1* | 7/2014 | Wexler ................... G01C 11/04 382/106 |
| 2015/0009312 | A1 | 1/2015 | Verna et al. |
| 2015/0052008 | A1 | 2/2015 | Campbell |
| 2015/0228084 | A1 | 8/2015 | Belyaev |
| 2015/0245016 | A1* | 8/2015 | Atac .................. G02B 27/0172 348/47 |
| 2016/0212342 | A1* | 7/2016 | Semenov ............... H04N 5/357 |
| 2016/0223316 | A1* | 8/2016 | Jordil .................. G01B 11/005 |
| 2016/0286906 | A1 | 10/2016 | Malal |
| 2016/0292920 | A1* | 10/2016 | Sprock .................... G06T 11/60 |
| 2016/0343176 | A1* | 11/2016 | Ackley ..................... G06K 9/18 |
| 2017/0046773 | A1* | 2/2017 | Hendricks, II ..... G06Q 30/0635 |
| 2017/0169571 | A1 | 6/2017 | Hung |
| 2018/0035762 | A1 | 2/2018 | Towns |
| 2018/0160777 | A1 | 6/2018 | Hei |

FOREIGN PATENT DOCUMENTS

| | | |
|---|---|---|
| CN | 1679478 | 10/2005 |
| CN | 1795813 | 7/2006 |
| CN | 1821715 | 8/2006 |
| CN | 1933778 | 3/2007 |
| CN | 102102978 | 6/2011 |
| CN | 201867174 | 6/2011 |
| CN | 102165492 | 8/2011 |
| CN | 102494616 | 6/2012 |
| CN | 102519373 | 6/2012 |
| CN | 103063617 | 4/2013 |
| CN | 103499303 | 1/2014 |
| CN | 103608666 | 2/2014 |
| CN | 103829928 | 6/2014 |
| CN | 1267501 | 9/2019 |
| DE | 8030534 | 7/1981 |
| EP | 1210908 | 6/2002 |
| GB | 2384425 | 1/2005 |
| JP | H04073052 | 3/1992 |
| JP | 2002224086 | 8/2002 |
| JP | 2008241256 | 10/2008 |
| JP | 2013062692 | 4/2013 |
| JP | 2013153408 | 8/2013 |
| JP | 2014500999 | 1/2014 |
| JP | 2014183565 | 9/2014 |
| JP | 2014522500 | 9/2014 |
| JP | 2018532205 | 11/2018 |
| KR | 1020140015780 | 7/2014 |
| KR | 1020150018973 | 2/2015 |
| KR | 101506685 | 3/2015 |
| WO | WO2007025350 | 3/2007 |
| WO | WO2012059851 | 5/2012 |
| WO | WO2012174182 | 12/2012 |
| WO | WO2017072008 | 5/2017 |
| WO | WO2018109421 | 6/2018 |

OTHER PUBLICATIONS

Hajime Sato, Preliminary study of hair form of Japanese head hairs using image analysis, Forensic Science International, Jan. 1, 2003, pp. 202-208; XP055077513, vol. 131 No. 2-3.
Kasturi R. et al., System for Interpretation of Line Drawings, IEEE Transactions on Pattern Analysis & Machine Intelligence, Oct. 1, 1990, pp. 978-992, XP000159051, vol. 12, No. 10, US.
Scott Highton, Virtual Reality Photography: Creating Panoramic and Object Images, Internet Article, Feb. 2, 210, p. 202; XP055263817.
Xu et al., Fiber Cross-Sectional Shape Analysis Using Image Processing Techniques, Textile Research Journal, Dec. 1, 1993, pp. 717-730, XP055268166, vol. 63, No. 12, US.
Wenzel Jakob et al., Capturing hair assemblies fiber by fiber, ACM Transactions on Graphics, 2009, pp. 164:1-164:9; XP055263403; XP058103955, vol. 28, No. 5, ACM Pres, New York.
Shinobu Nagase et al., Changes in structure and geometric properties of human hair by aging, J. Cosmetic Science, Nov. 1, 2009, pp. 637-648; XP055263417, vol. 60.
Search Report and Written Opinion in PCTEP2016075138, dated Jan. 17, 2017.
Search Report and Written Opinion in PCTEP2016075136, dated Nov. 29, 2016.
Search Report and Written Opinion in EP15192432, dated May 12, 2016.
Search Report & Written Opinion in EP15192434, dated Apr. 25, 2016.
Co-Pending Application, Abid Iftikhar, Filed April 12, 2018.
Search Report in EP15169995; dated Nov. 13, 2015.
Written Opinion in EP15169995; dated Nov. 13, 2015.
IPRP1 in PCTEP2016061345; dated Dec. 5, 2017.
Search Report and Written Opinion in PCTEP2016061345; dated Jul. 27, 2016.
L'oreal; tin. https://play.google.com/store/apps/details?id=com.modiface.loreal.stylemyhair; Before filing of application.
Schwarzkopf; http://www.schwarzkopf-professional.co.uk/skp/uk/en/home/products/colour/house-of-color.html; Before filing of application.

(56) References Cited

OTHER PUBLICATIONS

Schwarzkopf; http://www.schwarzkopf-professional.co.uk/skp/uk/en/home/products/care/hair-expert-app.html; Before filing of application.

* cited by examiner

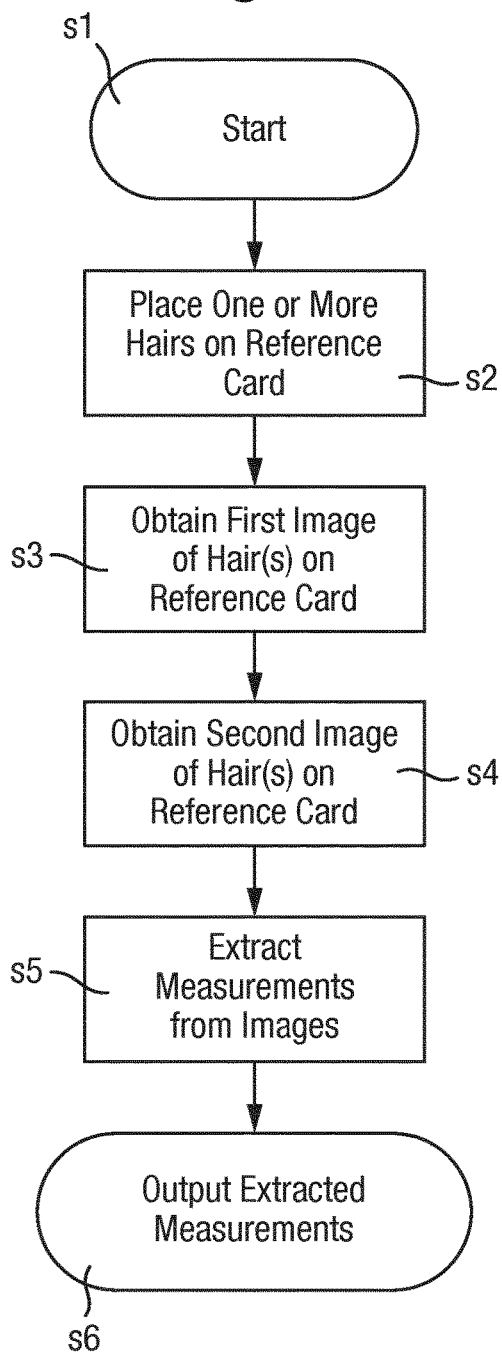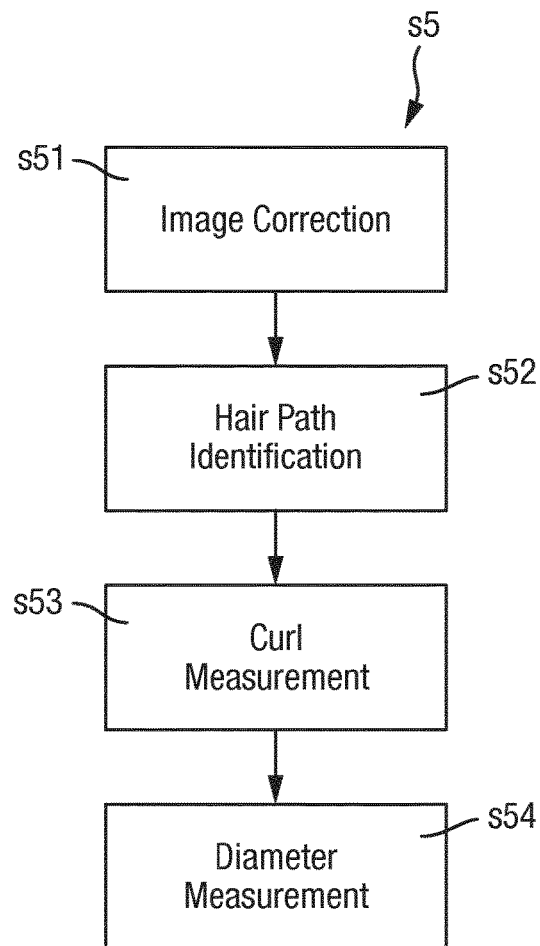

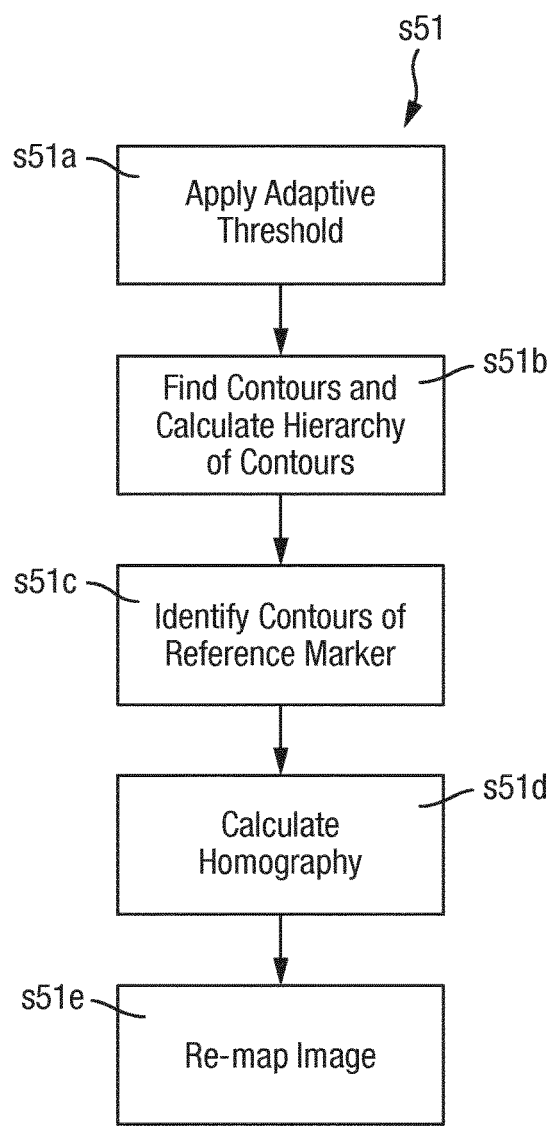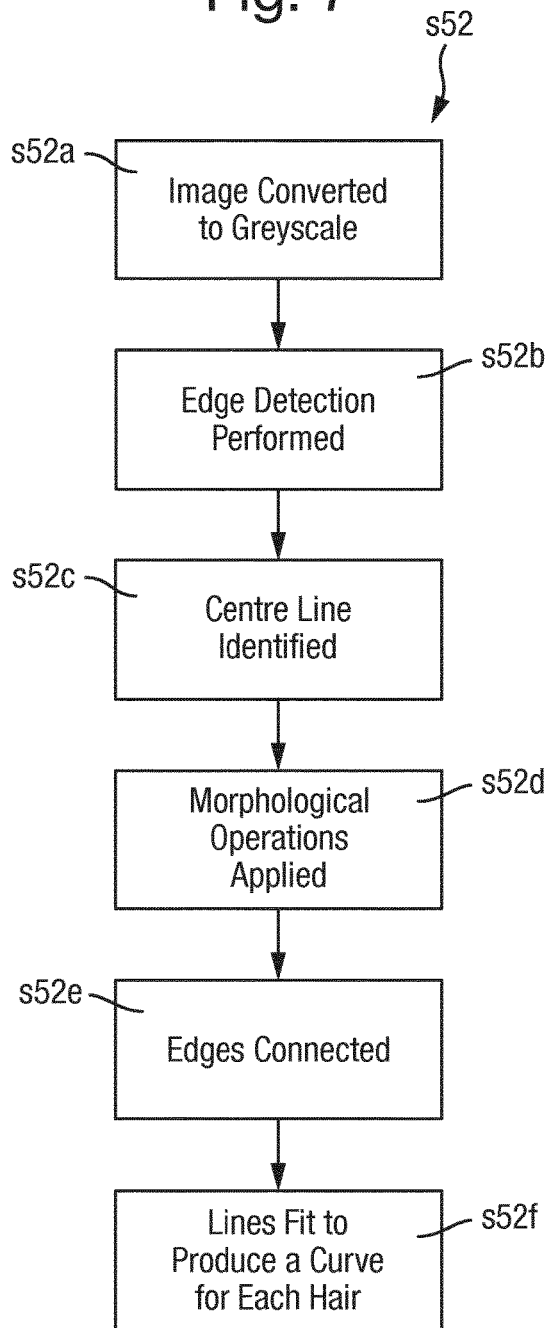

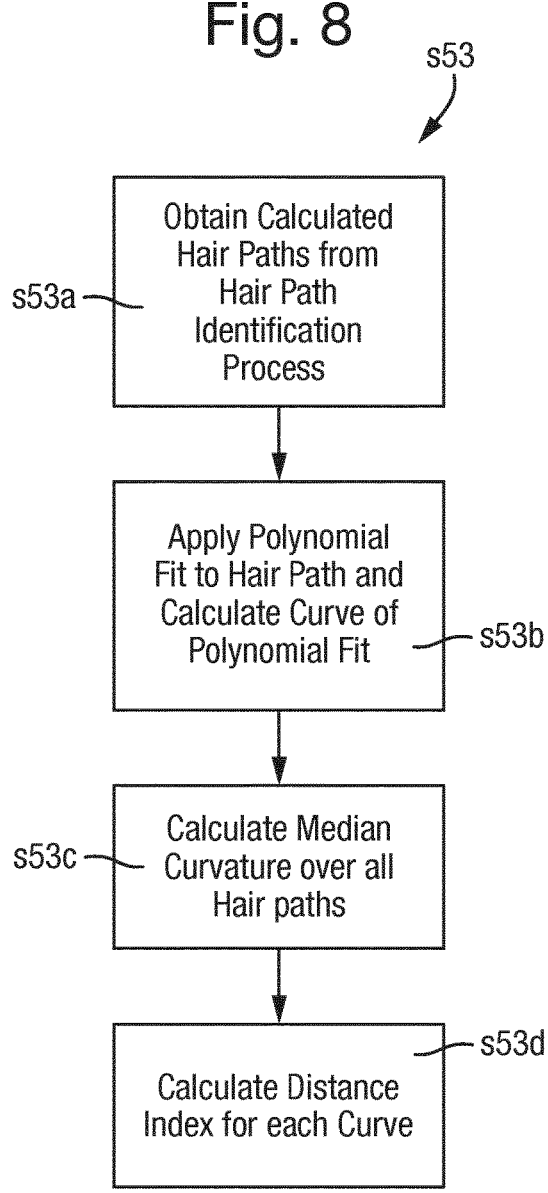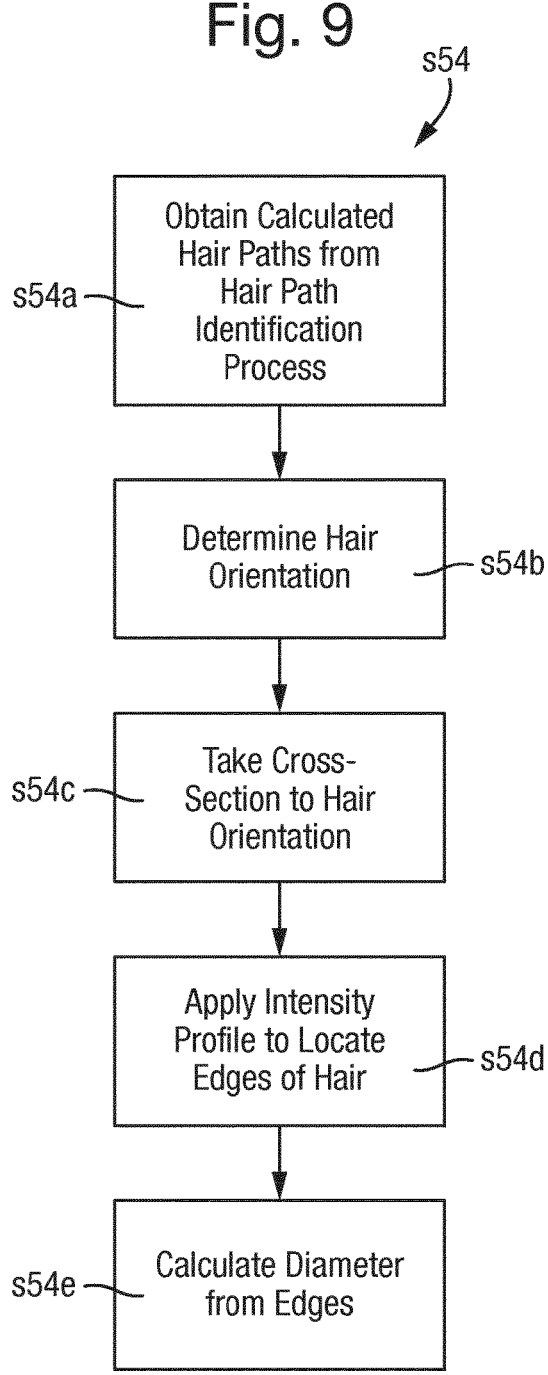

Fig. 22
$$\text{Curl Index} = \frac{\text{Maximum Extent}}{\text{Path Length}}$$
$$\text{Mean Distance Index} = \frac{4 \times \text{Median Distance From Centre}}{\text{Path Length}}$$
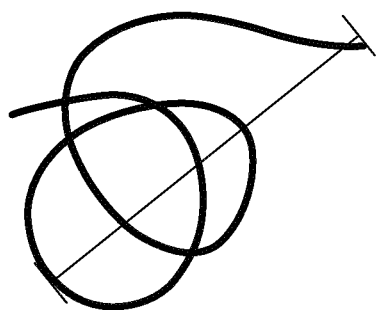
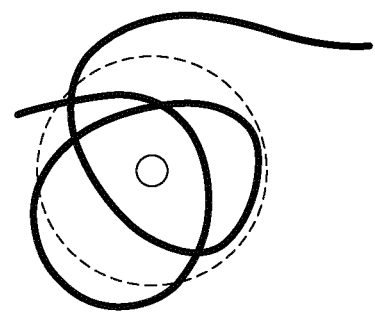
Maximum Extent          Median Distance $$\text{Curl Index} = \frac{\text{Maximum Extent}}{\text{Path Length}}$$

$$\text{Mean Distance Index} = \frac{4 \times \text{Median Distance From Centre}}{\text{Path Length}}$$

Maximum Extent            Median Distance

Fig. 27

| Category | Diameter Range (μm) |
|---|---|
| 1 | <50 |
| 2 | 50 - 60 |
| 3 | 60 - 70 |
| 4 | 70 - 80 |
| 5 | 80 - 90 |
| 6 | 90 - 100 |
| 7 | 100 - 110 |
| 8 | 110 - 120 |
| 9 | 120 - 130 |
| 10 | >130 |

HAIR DIAMETER MEASUREMENT

FIELD OF THE INVENTION

The present invention relates to a system and method for measuring indications of hair type of a user, more particularly to a system for measuring the diameter of a hair, the system comprising a mobile device and a reference card.

BACKGROUND OF THE INVENTION

Consumers of hair products are able to select from a high volume of available products, due in part to the fact that many hair care brands have increasingly large product ranges.

These product ranges may cover various product categories including: shampoos, conditioners, treatments and styling products. Within each product category, a brand may produce multiple versions of a product with the ingredients of each version chosen to address the particular needs of a given target hair type. For example, a given hair type may include one or more of the following: straight hair, wavy hair, curly hair, thick hair, frizzy hair, thin hair, colour treated hair, and damaged hair.

Each version of a product could be clearly marketed for its target hair type. However, it may be difficult for a consumer to accurately identify what hair type they actually belong to and the vast array of choice could therefore lead to confusion. When a consumer chooses a version of a product, their choice is usually based on nothing more than their own perception of their hair type and this perception may be inaccurate particularly if it is based on external factors such as advertising or relative comparisons with friends and family. In addition, terms such as "thick hair" or "thin hair" can be open to misinterpretation. For example, a consumer may have many hair strands, but each hair strand may be of a thinner than average diameter.

The optimal choice for hair products could depend on how a consumer styles their hair. For example, a consumer may have naturally curly hair but may blow dry their hair straight. In such a scenario, the consumer may find it difficult to categorise their own post-styling hair type. They could consider it to be curly, straight, or somewhere in-between.

In the current market, it is therefore easy for consumers to wrongly assign themselves a specific hair type and to select a specific version of a product, the ingredients of which may not be the best match for the actual characteristics of their hair. Such selection of a less than optimal product version can lead to poor customer satisfaction.

There is therefore a need for consumers of hair products to be able to make more accurate, more informed choices about what version of a haircare product is best for them.

SUMMARY OF THE INVENTION

While it is possible to gain a macroscopic appreciation of characteristics such as hair thickness and curvature using the naked eye or conventional optical microscopes, such examination is invariably unreliable due, for example, to variations in the eyesight of different users. So, choosing a haircare product based on such a macroscopic examination is unlikely to lead to the optimal choice of haircare product, and resultant customer satisfaction. At its broadest, the present invention addresses this problem by providing a more reliable, and easily-usable method/system for measuring indications of the hair type of a user, which do not rely on the user's discernment. Focused haircare recommendations can therefore be automatically provided, in a manner which requires minimal human input, and the scheme of provision for which does not vary from user to user.

The present invention achieves this by providing, according to a first aspect, a method of measuring indications of hair type of a user, the method comprising the steps of: providing a mobile device; providing a reference card, the reference card including one or more reference markers; providing one or more of the user's hairs at the surface of the reference card; acquiring one or more images of said one or more hairs using the mobile device; identifying the path of each of the one or more hairs along the reference card; and calculating the diameter of each hair from the acquired image.

In this way, the first aspect of the invention may provide a method of measuring indications of a hair type of a user using a mobile device, and a reference card including one or more reference markers, the method including the steps of:
 providing one or more of a user's hairs on the surface of the reference card;
 acquiring one or more images of said one or more user's hairs using the mobile device;
 identifying the path of each of the one or more hairs along the reference card; and
 calculating the diameter of each hair from the acquired image.

In the present application, the term "hair type" may be understood amongst other things to refer to the thickness or diameter of the hair, or the curvature, curve or curl of the hair (such terms may be used interchangeably).

Accordingly, the curve or curl of the hair may also be calculated from the identified path, in addition to the calculation of the diameter. By calculating these from acquired images, better results may be achieved than the very coarse estimates of thickness and curvature of a hair which a user may be able to provide themselves without employing the method of the first aspect of the present invention, e.g. just by examining the hair by eye.

The step of providing one or more of a user's hairs on the surface of the reference card may include simply placing the card on the surface of the reference card. In methods according to the present invention, as discussed later, there is no requirement for securing the hair flat on the surface, which may distort calculations relating to both diameter and curve of a given hair.

The image acquired may include a plurality of pixels, each having an associated light intensity value. The image includes the geometric profile of each hair on the surface of the reference card, which represents the shape of that hair within the image, and may be detected using the light intensities of the pixels within the image. In other words, each hair has an associated geometric profile within the acquired image. The geometric profile of the hair may be considered to include path information (or "the path") and dimensional information (or "dimensions"). Dimensional information preferably includes the diameter or thickness of the hair in question. The path represents the direction of a given hair at all points along its length, or in other words the route which a given hair takes through the image. Path information and dimensional information are preferably separable.

Accordingly, the diameter of the hair may be calculated from the geometric profile of the hair. The identified path is also useful in the calculation of the diameter of the hair. Consider, for example, a curly hair, which crosses over itself in the acquired image, i.e. where the path of the hair crosses itself. Here, identification of the path of the hair ensures that it is known that there is only one hair which crosses itself, rather than several hairs crossing each other. Thus, the identification of the path of the hair ensures that superfluous diameter calculations are not performed. A similar situation occurs when there are more than one hairs present on the reference card. Here, identification of the path of each hair ensures that diameter calculations are performed for each hair, so that neither too few nor too many calculations are performed. In the two preceding examples, once the path has been identified the calculation of the diameter may be performed from the geometric profile of each respective hair.

As will be appreciated from the above, no alignment of the one or more hairs is necessary, and when a plurality of hairs are used, it does not matter if there is any overlap or crossing of hairs. Nor does it matter if a single hair crosses over itself, due to the path identification step of the present invention.

In this way, the claimed system provides a simple yet accurate mechanism for quantitative analysis of the hair. By taking actual measurements, the consumer is more likely to correctly identify their hair type. As a result, based on this identification, they are more likely to choose the optimal product for their hair as errors which arise from qualitative descriptions of hair types can be prevented. The likelihood of customer satisfaction is therefore increased.

Advantageously, the system can be implemented by the user themselves at home and does not require any complicated or expensive laboratory equipment.

The reference markers on the reference card allow for calibration of the image, particularly with regard to the dimensions of the hair.

For example, the reference markers may indicate a known dimension which may then be used in subsequent image processing, particularly in the calculation of the diameter of the hair. Specifically, calculation of the diameter of the hair may include a comparison of the diameter of the hair in the acquired image (e.g. from the geometric profile), with a known dimension indicated by the reference marker(s). Accordingly information regarding the reference marker is preferably used in the calculation of the diameter, or other geometric properties. Other beneficial features of the reference markers are set out later in the application, with reference to other structural and functional features of the invention.

Optional features of the invention will now be set out. These are applicable singly or in any combination with any aspect of the invention.

Advantageously, there is no need for the reference card to include any kind of attachment portions or adhesive region(s). This is particularly advantageous for the diameter measurement of curly hair because curly hair has an inherent resilience and it may therefore more difficult to attach to the card.

The step of acquiring the image may involve a refocusing step if image appears to be out of focus on the device.

Acquiring the one or more images may be performed simply by holding the mobile device above the reference card, and actuating an image capture function perhaps using a dedicated button or a touchscreen element of the mobile device.

The mobile device may comprise a digital imaging device (e.g. a camera) for capturing the image of the one or more hairs on the reference card. In this way, the mobile device is configured to capture the image as well as to acquire and process it. In addition to the digital imaging device, the mobile device may include a display.

The display may be configured to display acquired images captured using the digital imaging device. The mobile device may include a database storing a library of images, and preferably the mobile device may be configured to store images acquired using the digital image capturing device in the database. The mobile device may be configured to retrieve images from the database for further processing, where said further processing may include any method steps disclosed herein which are performed subsequently to the step of acquiring one or more images of the one or more hairs.

Optionally, the step of acquiring the one or more images includes the steps of: providing a real time view (e.g. on the display) of the input of a digital imaging device on the mobile device; providing an overlay on top of the real time view, the overlay having the same shape as one or more of the one or more reference markers.

When the overlay has the same shape as the reference markers, this ensures that the user is able to position the mobile device such that the overlay overlaps the reference marks shown in the real time view. Consequently, a desired alignment may be achieved as the image is acquired. By lining up the overlay with the reference marks in the real time view, both a desired orientation and a desired distance from the reference card can be achieved. Clearly, this is advantageous since such an orientation/distance can be selected which provides a desirable resolution for the acquired image, or which allows a wider field of view, (i.e. making sure that the one or more hairs are shown fully in the acquired image). Accordingly, in some embodiments of the method, the entirety of each of the one or more of the user's hairs is provided within one or more of the reference marks, i.e. no part of any hair lies outside one or more of the reference markers.

Optionally a first overlay is provided for alignment with a first reference marker during a first image capture step and a second overlay is provided for alignment with a second reference marker during a second image capture step.

Optionally, the step of acquiring an image of said one or more of the user's hairs includes: obtaining a first image of the one or more hairs on the reference card, the first image being taken at a first distance from the reference card; and obtaining a second image of the same one or more hairs on the reference card, the second image being taken at a second distance from the reference card; wherein the second distance is less than the first distance.

By taking two images at different distances, different levels of zoom are achieved. A more zoomed-in image, i.e. the second image provides a closer view of the one or more hairs and accordingly may provide a higher resolution which may be advantageous for e.g. identification of edges within the image, or calculation of diameter from the image (or the geometric profile). Similarly, a close-up image from the second distance may also allow more accurate determination of the path of the one or more hairs shown within the second image.

In contrast, the first image from the (larger) first distance allows a wider field of view. In this way, the first image will contain a greater proportion, and preferably all, of each of the one or more of the user's hairs. This enables the path to be identified over a greater length of each respective hair. By maximizing the extent of the hair which is in the image, it is possible to ensure with more certainty that the correct number of hairs is identified (taking into account e.g. hairs crossing over themselves and over other hairs). This is also particularly useful in embodiments in which the curve of the hair is also calculated, since there is more data (i.e. data over a greater length) available for each respective hair.

In some embodiments, the first reference marker is for use with the first image (at the first distance), and the second reference marker is for use with the second image (at the second distance). The reference markers in this case may be associated with the first and second overlays, as discussed earlier. The presence of first and second reference markers ensure an appropriate alignment of the first image, relative to the second image. Again, here "alignment" refers to a combination of both the distance and the orientation. Specifically, it ensures an appropriate alignment of position of the mobile device when acquiring the first image, relative to the position of the mobile device when acquiring the second image. The size of the first reference marker may be selected so that, when it is aligned with the first overlay, the mobile device is at the first distance. Similarly, the size of the second reference marker may be selected so that, when it is aligned with the second overlay, the mobile device is at the second distance. The first and second distance may be predetermined, or user-set.

Similarly, the shapes of the first and second reference markers may be selected so that when they are aligned with the respective overlay, the mobile device is at the same orientation with respect to the reference card. This ensures that the images are acquired from the same direction, and therefore that the first and second image show a given hair or hairs with the same projection. Consequently, and importantly, this means that the geometric profile of the one or more hairs in the first and second image is the same, viewed only at a different level of zoom. This means that the path is substantially unchanged, and ideally completely unchanged, the second image relative to the first image. This is particularly important, since the one or more hairs need not be secured to the reference card, and accordingly the projection from slightly different angles may be substantially different.

As discussed, a given hair type may include one or more of the following: straight hair, wavy hair, curly hair, thick hair, frizzy hair, thin hair, colour treated hair, and damaged hair To provide an improved accuracy when identifying hair type, it may be desirable to measure more than one indication of the type of hair. For example, the method of the present invention may measure one or more characteristics of the curl of a user's hair as well as other indications such as the diameter of their hair. Knowledge of multiple indications of hair type is particularly useful when choosing suitable hair products. For example, products best suited for straight thick hair may not be optimal for thin curly hair, thick curly hair, or thin straight hair.

Curl algorithms for calculating the curl of a hair from an image may give the best results when more of the length of the curl lies within the image. Other algorithms such as those used to calculate diameter, may give the best results when the numbers of pixels per hair diameter are maximised. Thus, where measurements of multiple indications of the hair type are desired, overall results can be improved by obtaining two separate images; one taken over a larger capture area and one close up. The close up that forms the second image is preferably taken of a zoomed in region within that capture area.

Optionally, the reference card comprises: a first reference marker for aligning the mobile decide with the reference card when obtaining the first image; and a second reference marker for aligning the mobile device with the reference card when obtaining the second image.

The first reference marker may take the form of an outer marker for example a rectangle or other polygon. One advantage of a rectangular marker is that it can be formed of the same relative dimensions as the screen of a mobile device which optimises the total pixels available on the mobile device.

The first reference marker may be a solid line around the perimeter or separated from the perimeter of the reference card to form a boarder.

The reference card could be provided as part of marketing material, for example on an advert or article in a magazine.

Optionally, a plurality of the user's hairs are provided at the surface of the reference card.

A single hair can be measured. However, measuring multiple hairs may give more consistent readings due to variation between hairs from a person's head Optionally, at least three of the user's hairs are provided at the surface of the reference card.

Optionally, the image(s) obtained of the hairs is a single image comprising all three hairs. Where a first and a second image are taken, the hairs are not moved in-between the two images.

Identifying the path of a given hair refers to the identification of the path in the geometric profile of that hair in the image acquired by the mobile device. Identification of the geometric profile may include an initial step of detecting the location of the hair in the acquired image. Such a detection may be based on the light intensity value of pixels within the acquired image. When the location of the hair is detected, the path which it forms may be parameterized, for example using a polynomial fit. However, there are numerous other examples of methods by which the path of the hair may be identified.

For example, in other embodiments, the step of identifying the path of each of the one or more hairs along the reference card may comprise: applying an edge detection algorithm to the image; identifying the centre line of the one or more hairs at a plurality of points along the hairs; and applying a fit to the plurality of points.

Optionally, the step of applying a fit to the plurality of points includes the step of applying a polynomial fit.

Optionally, the method of measuring indications of hair type of a user further comprises the step of extracting the curl of the one or more hairs from the one or more acquired images.

Optionally, the step of calculating the diameter of each hair from its identified path includes: measuring the orientation of at least a given point on the identified path; and taking a cross section perpendicular to the orientation of the path.

Optionally, the step of taking a cross section perpendicular to the orientation of the path includes: taking an intensity profile along a direction perpendicular to the orientation of the path; locating two peaks on the intensity profile corresponding to two opposite edges of the hair; and measuring the diameter of the hair at that point of the path as the maximum between the two peaks.

According to a second aspect of the present invention, there is provided a system for measuring the hair type of a user, the system comprising: a mobile device (20); and a reference card (10), the reference card including one or more reference markers; wherein the mobile device is configured to: acquire one or more images, each of the one or more images being an image of one or more hairs of the user; identify the path of each of the one or more hairs along the reference card; and calculate the diameter of each hair from its identified path.

The configuration of the mobile device to convert the image(s) into hair measurements may take the form of a computer program product, tangibly embodied in a non-transitory computer readable medium, the computer program product including instructions for carrying out the method steps of the first aspect required to turn the image taken by a digital imaging device of the mobile device into the hair indication measurements such as curl and/or diameter.

For example, the computer program may be an app which is downloadable onto a mobile device.

The term "mobile device" may be understood to mean "portable electronic device", specifically a portable electronic device configured to receive a visual input. Accordingly, the mobile device could be any electronic device such as: mobile phone/cellphone, tablet, phablet, laptop or a digital camera. As was discussed earlier in the application, the mobile device may comprise a digital imaging device (e.g. a camera) for capturing the image of the human hair attached to the reference card. In this way, the mobile device is configured to capture the image as well as to process it.

The surface of the reference card may be coloured white to make the colour contrast as great as possible between the hair to be measured and the card surface. A white surface would be particularly optimised for dark hairs (e.g. brown, black). For blond or grey hairs it may be preferable to include a dark surface to invert the colour contrast. A single reference card may be configured to be used with multiple hair colours by including a surface with a while background and a surface with a black background. White and black are used as examples, but could be substituted by other light or dark colours.

Optionally the reference card may contain instructions on its use or on the applications use. It may also contain a website link and/or instructions for downloading the computer program (application) for carrying out the claimed method.

Optionally the reference card has a matt surface. This surface may have a roughness more than or equal to the roughness of matt printer paper. This may correspond to a TAPPI 75 gloss value below 35%, even more preferably this may correspond to a TAPPI 75 gloss value of no more than 10%.

In this way, the amount of light absorbed by the card is increased. Reflections of light from the card are therefore minimised so that light spots in the image due to reflections of light sources are reduced. This is particularly important when the image is taken in artificial light. Bright spots in the image can affect the processing of the image so a matt surface of the reference card gives rise to a robust system that can be used in various lighting conditions or changing lighting conditions.

Where images are recorded in well-lit environments, it is particularly desirable for any flash on the mobile device to be disabled before an image is recorded. Where a flash might be useful (for example in an extremely poorly lit environment) the matt surface will help to minimise the effect of bright spots which arise as a result of the reflection of the flash.

Optionally, the reference card comprises: a first reference marker for aligning the mobile decide with the reference card when obtaining a first image using the mobile device; and a second reference marker for aligning the mobile device with the reference card when obtaining the second image using the mobile device.

In some embodiments the size and/or shape of the reference card itself may be used as a reference marker instead of or in addition to a calibration marker. The measurements of the reference card could include the height, length or any other measurement of a part the reference card such as distance between diagonally opposing corners.

Optionally, the second reference marker is located within the first reference marker. This may, for example, ensure that the second image is taken at a smaller distance than the first image as is discussed earlier.

Optionally, the mobile device is configured to present the image taken by the digital imaging device to the user for quality verification before processing the image.

According to a third aspect of the present invention there is provided a reference card for use with a computer program to measure indications of hair type of a user, the reference card including: a first reference marker for aligning the mobile decide with the reference card when obtaining a first image using the mobile device; and a second reference marker for aligning the mobile device with the reference card when obtaining the second image using the mobile device; wherein the second reference marker is located within the first reference marker. Such a reference card may be used in the method of the first aspect of the invention.

According to a fourth aspect of the present invention, there is provided a computer program for measuring indications of hair type of a user, the computer program configured to carry out the steps of: acquiring one or more images of one or more hairs on a reference card using a mobile device; identifying the path of each of the one or more hairs along the reference card; and calculating the diameter of each hair from its identified path.

Optionally, the step of acquiring the one or more images includes the steps of: providing a real time view of the input of a digital imaging device on the mobile device; providing an overlay on top of the real time view, the overlay having the same shape as one or more of the one or more reference markers.

In this way an alignment aid is provided to ensure that the images acquired are taken at a suitable distance and angle such that the resolution will be sufficient and no parallax error will be introduced.

Where compatible, optional features set out above with respect to the first aspect of the invention may also be included in any or all of the second, third and fourth aspects of the invention, and vice versa.

Further optional features of the invention are set out below.

BRIEF DESCRIPTION OF THE DRAWINGS

Embodiments of the invention will now be described by way of example with reference to the accompanying drawings in which:

FIG. 4 shows a process for measuring the hair type of a user;

FIG. 5 shows a process for extracting measurements from images;

FIG. 6 shows an example of image correction steps carried out as part of the process for extracting measurements from images;

FIG. 7 shows an example of hair path identification steps carried out as part of the process for extracting measurements from images;

FIG. 8 shows an example of curl measurement steps carried out as part of the process for extracting measurements from images;

FIG. 9 shows an example of diameter measurement steps carried out as part of the process for extracting measurements from images;

FIG. 22 depicts alternative examples of measurements of some characteristics of curl;

FIG. 27 gives an example of diameter ranges for characterisation.

DETAILED DESCRIPTION AND FURTHER OPTIONAL FEATURES OF THE INVENTION

Figure 1:
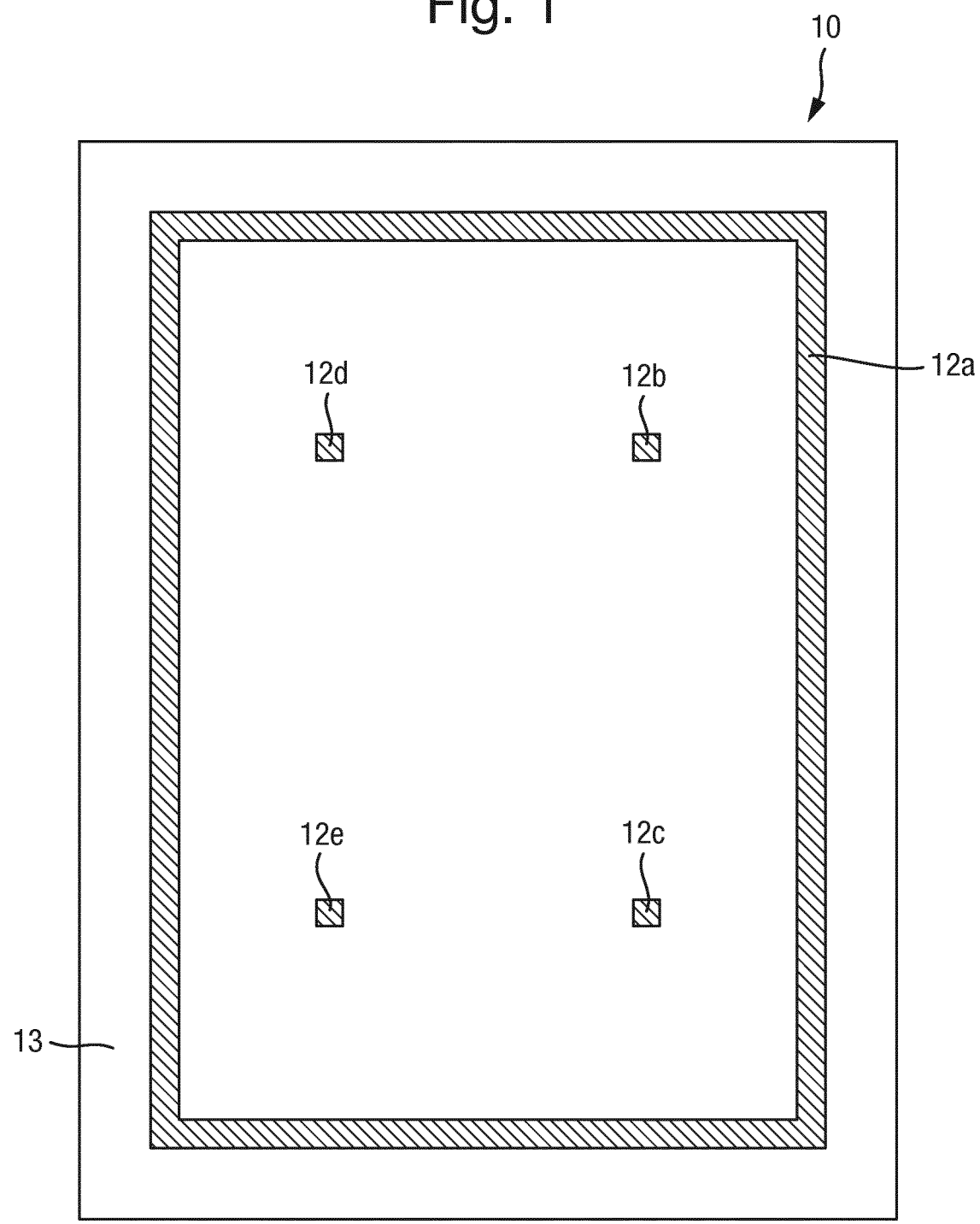
FIG. 1 shows a schematic diagram of a reference card.

A system for measuring the indications of hair type of a user is described with reference to FIGS. 1 to 3 below.

The system comprises a mobile device 20 and a reference card 10, the reference card comprising a first reference marker 12a and a second reference marker 12b, 12c, 12d, 12e on the card.

The first reference marker 12a forms an outer reference marker. In the embodiment shown in FIG. 1, this is a rectangle. The relative dimensions (i.e. the ratio between the length and the width) of the rectangle are the same as the relative dimensions of the perimeter of the reference card. They are also the same as the relative dimensions of the screen on the mobile device (i.e. of the array of pixels of the digital image device).

The second reference marker is formed from a plurality of separate reference markers arranges in an array. In this case, the second reference marker comprises four separate filled in squares, all four of the squares arranged in a rectangular array, the array lying within the first reference marker.

The outer points of the array of the plurality of separate reference markers would, if joined up, form corners of a rectangle having the same relative dimensions as that of the first reference marker.

The reference card 10 includes a surface 13 against which the hair should be located before measurement takes place. In the embodiment of FIGS. 1 to 3, the surface is a light colour such as white in order to maximise contrast between it and dark hairs placed upon it (e.g. brown or black hairs).

Figure 2:
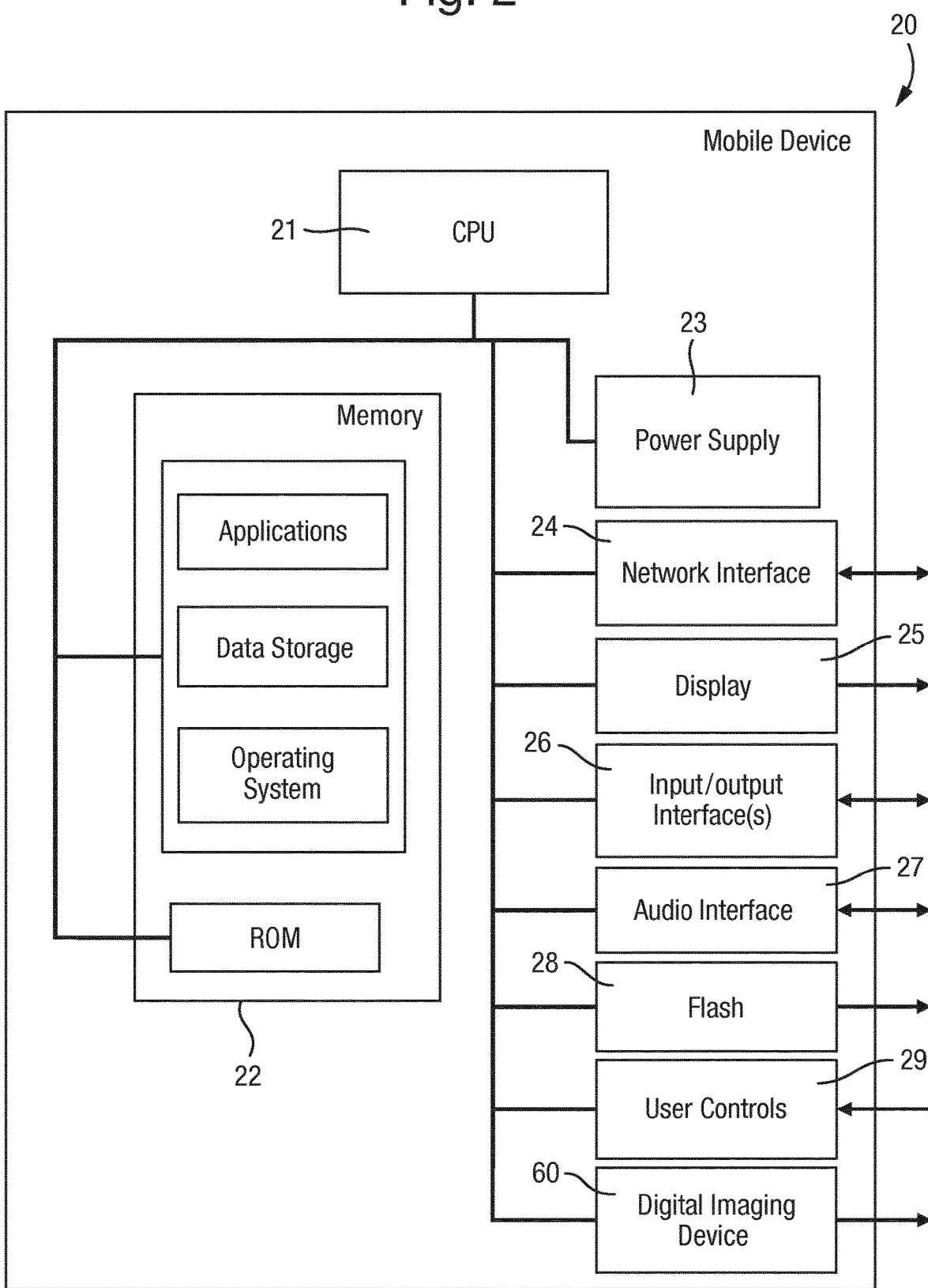
FIG. 2 shows a schematic diagram of a mobile device.

FIG. 2 shows an illustrative embodiment of a mobile device which is suitable for practicing the various aspects and embodiments of the present invention. The mobile device may include all of the components shown but may contain more, or less.

The mobile device 20 includes a digital imaging device 60 such as a digital camera for recording digital photographs. These photographs may then be stored in a data storage section of the memory 22.

The mobile device 20 shown includes a central processing unit (CPU) 21 in communication with a memory 22 and various other components.

These other components of the mobile device 20 shown include a power supply 23, a network interface 24, a display 25, an input/output interface 26, an audio interface 27, a flash 28 and user controls 29.

The power supply 23 provides the power used by the mobile interface and may take the form of a rechargeable battery and/or external power source.

The network interface 24 provides a mechanism for the mobile device to communicate directly or indirectly with any other computing device and includes circuitry configured for use with one or more communication protocols and technologies including but not limited to: GPRS; GSM; TDMA; transmission control protocol/Internet protocol (TCP/IP); CDMA; WCDMA; Wi-Fi; 3G, 4G, Bluetooth or any other wireless communication protocols.

The display 25 may be an LCD (Liquid crystal display), a plasma display or any other suitable electronic display and may be touch sensitive in that it may include a screen configured to receive an input from a human digit or a stylus.

Input/output interface(s) 26 may include one or more ports for outputting information e.g. audio information via headphones, but may also be an input port configured to receive signals including remote control signals.

The audio interface 27 typically includes a speaker which enables the mobile device to output signals and a microphone which enables the mobile device to receive audio signals including voice control inputs for use in controlling applications.

The mobile device 20 shown includes a flash 28 which may be used in conjunction with the digital imaging device to illuminate an object of which a photograph is being taken.

User controls 29 may take the form of external buttons or slider which allow a user to control various functions of the mobile device.

An application saved on the device may be configured to interact with the various components of the device such that upon receiving an input from one or more of the user controls, the digital imaging device and is triggered and a digital photograph is taken of an object (such as the hair on the reference card). This image may then be stored in the memory and one or more algorithms may be used to process the stored image.

The computer program described herein may take the form of an application stored in the memory 22.

The mobile device may be connected to an external computer 30 either directly or via a network 40 so that computationally extensive calculations can be carried out by a computational module on the external computer, the external computer being more powerful than the mobile device and therefore capable of performing the calculations more quickly.

The mobile device 20 may also be configured to exchange information with other computers via a network 40. The network may include the internet and/or one or more local area networks (LANs) or wide area networks (WANs).

Figure 3:
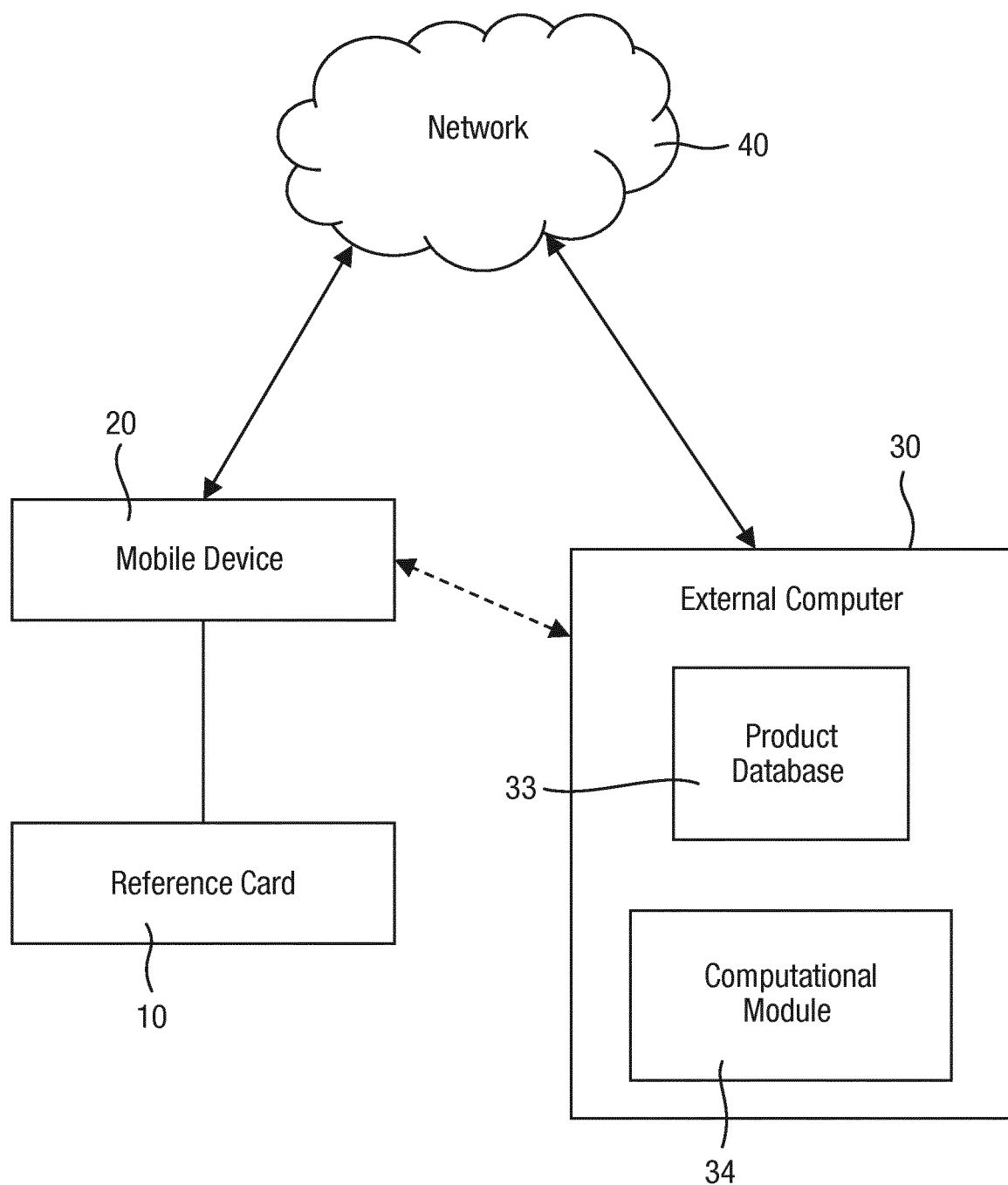
FIG. 3 shows a schematic diagram of a mobile device and reference card in communication with a network.

As shown in FIG. 3, this exchange of information may include accessing a product database 33 on an external computer 30. The product database may include a list of suitable products and an indication of the diameter of hair for which the product is most suitable. This indication could be an upper diameter threshold, a lower diameter threshold, or a range of suitable diameters.

In this way, processed information extracted from an image taken of a user's hair on the reference card 10 can be compared and matched against the indication in the product database. Selection criteria can then be applied to select the most suitable product for the user based on the numerical value or label.

In other embodiments, the product database may be stored within the memory 22 of the mobile device.

It should be understood that information such as the measurements taken and/or product selection can be communicated with external servers via the network 40. For example, the user could share this information with others by posting the information on social media websites.

A method of measuring indications of hair type of a user is described below with reference to FIGS. 4 to 17, where like reference numerals correspond to features described in relation to FIGS. 1 to 3.

A reference card 10 is provided along with a mobile device 20. The hair to be measured is placed s2 onto the reference card 10 so that the hair lies against the surface 13 of the reference card. The direction of the placement of the hair is not important. Hairs can simply be dropped onto the reference card. This step is shown in more detail in FIG. 10.

A first image of the hair on the reference card is taken (s3) using the digital imaging device 60 of the mobile device. The first reference marker 12*a* is used to align the image. This ensures that the image is taken at a first distance.

A second image of the hair on the reference card is taken (s4) using the same digital imaging device 60 of the same mobile device. The second reference marker in the form of the plurality of separate markers 12*b*, 12*c*, 12*d*, 12*e* is used to align the image. This ensures that the image is taken at a second distance which is less than the first distance.

The image(s) may be stored in the memory 22 before being processed.

Once the images have been acquired, measurements are extracted s5 from them.

As discussed in relation to FIGS. 5 to 9 below, the extraction of the measurements includes the steps of identifying the path of each of the one or more hairs along the reference card; and calculating the curve, diameter and other indications of each hair from its identified path.

FIG. 5 shows an overview of a process (s5) for extracting measurements from images. The process in the example shown comprises four main stages:

Image correction (s51);
Hair path identification (s52);
Curl measurement (s53); and
Diameter measurement (s54).

The portions of the algorithm which correct the image and detect the path of the hair are shared, the calculation of curve and diameter from the path are separate, as described in more detail below.

FIG. 6 shows an example of the image correction stage (s51).

Firstly, an adaptive threshold is applied to the image (s51*a*).

Contours are then found in this threshold and the hierarchy of these contours is calculated (s51*b*).

Contours matching those expected for the first or the second reference marker are found (s51*c*).

In the example shown, the four found corners of the marker (either the first reference marker or the second reference marker), and the known size of the marker are used to calculate a homography; a mapping between the distorted image and the true size of the marker (s51*d*). The image is then remapped to appear with the marker undistorted with bicubic interpolation.

FIG. 7 shows an example of hair path identification stage (s53).

Firstly, the image is converted to grayscale (s52*a*) (for example by taking only the green channel from the optical input of the digital imaging device).

Edge detection is then performed (s52*b*. This could be achieved by applying Sobel filters.

The centre line of the hair is identified (s52*c*) as being the centre point of two strong parallel edges facing opposite orientations within a threshold distance.

Morphological operations such as "bridging" "closing" and "thinning" are then preformed on the centre points (sometimes referred to as candidate points) to improve the data and remove noise (s52*d*).

Connected components are used to join edges (s52*e*) which are touching (in a Moore neighbourhood sense) and are not at a junction (i.e. a crossover between two or more hairs).

Lines are fit (s52*f*) to provide a curve for each hair. This includes fitting to the pixels of the centre points to produce many "curve" each comprised of many straight line "segments". All the curves are compared to each other and are merged if their ends lie close together and are in similar orientation. Very short curves below a given length threshold are removed to avoid anomalous results. This produces a list of curves each composed of segments identified by the x and y co-ordinates of their ends. In an ideal case a single curve will correspond to a single hair path for a single hair.

FIG. 8 shows an example of curl measurement stage.

Firstly, for each curve the curvature is calculated at many points along its length (s53*a*), for each calculation:
 a. The adjacent points in a window are averaged using a Gaussian kernel
 b. A polynomial is fit (s53*b*) to the resulting points
 c. The curvature of the polynomial function is calculated
Secondly, the algorithm returns the median curvature over all curves (s53*c*)

Thirdly, the algorithm calculates the "distance index", for each curve (s53*d*):
 a. The mean point of the curve is calculated
 b. The distance of each segment from this mean point is calculated
 c. The median of all these distances is calculated
 d. The distance index is calculated as the ratio of the median calculated in c above to the arc length of the curve
 e. This number is then weighted by the length of the curve.

FIG. 9 shows an example of diameter measurement stage (s54). As with the curl measurement, this uses the data from the identified hair paths so these must first be obtained (s54*a*).

For each curve, the diameter is calculated at many points along it, this is done as follows:

The orientation of the hair is measured (s54b) from the hair path(s), and a cross section taken perpendicular to this (s54c).

Bicubic interpolation, or another suitable method is used to take an intensity profile (s54d).

The intensity profile is used to locate the edges of the hair (i.e. the hair width) (s54d). Two peaks are found in the intensity profile and the maximum of these are taken to be the diameter (s54e).

The median is taken of all these readings to give the average hair diameter. This could be the median over a plurality measurements on one hair, or over a plurality of measurements over more than one hair.

Unlike other known types of diameter measurement, there is therefore no need to have aligned or oriented the hair in a specific way relative to the hair card. This is particularly advantageous for diameter measurements of curly or unruly hairs which can be difficult to align. However it also provides an efficient measurement technique for hair of all types.

User operation in order to carry out the method can be understood with reference to FIGS. 10 to 17 where like reference numerals are used for the features described in FIGS. 1 to 3.

Figure 10:
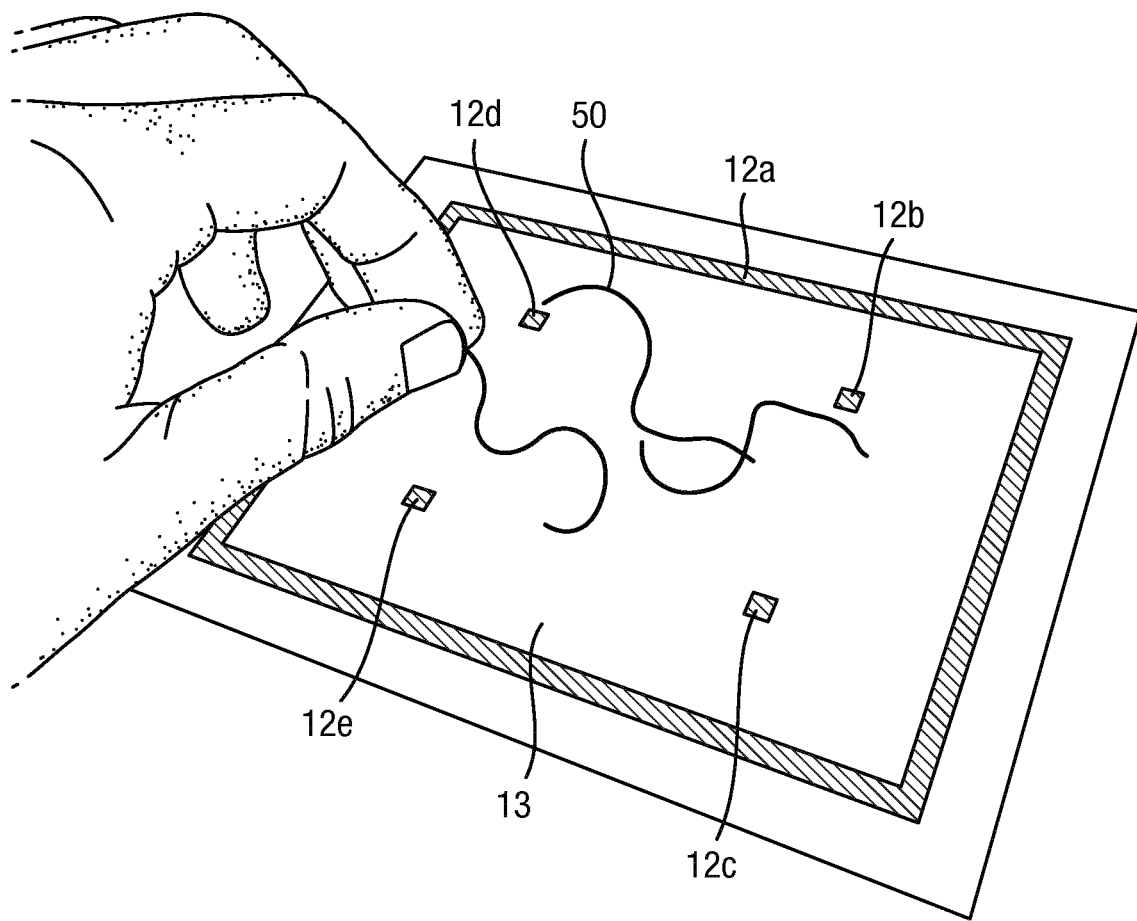
FIG. 10 shows an example of providing hairs to be measured at the reference card of FIG. 1.

FIG. 10 shows an example of providing hairs to be measured at the reference card of FIG. 1 by placing the plurality of hairs onto the reference card.

Figure 11:
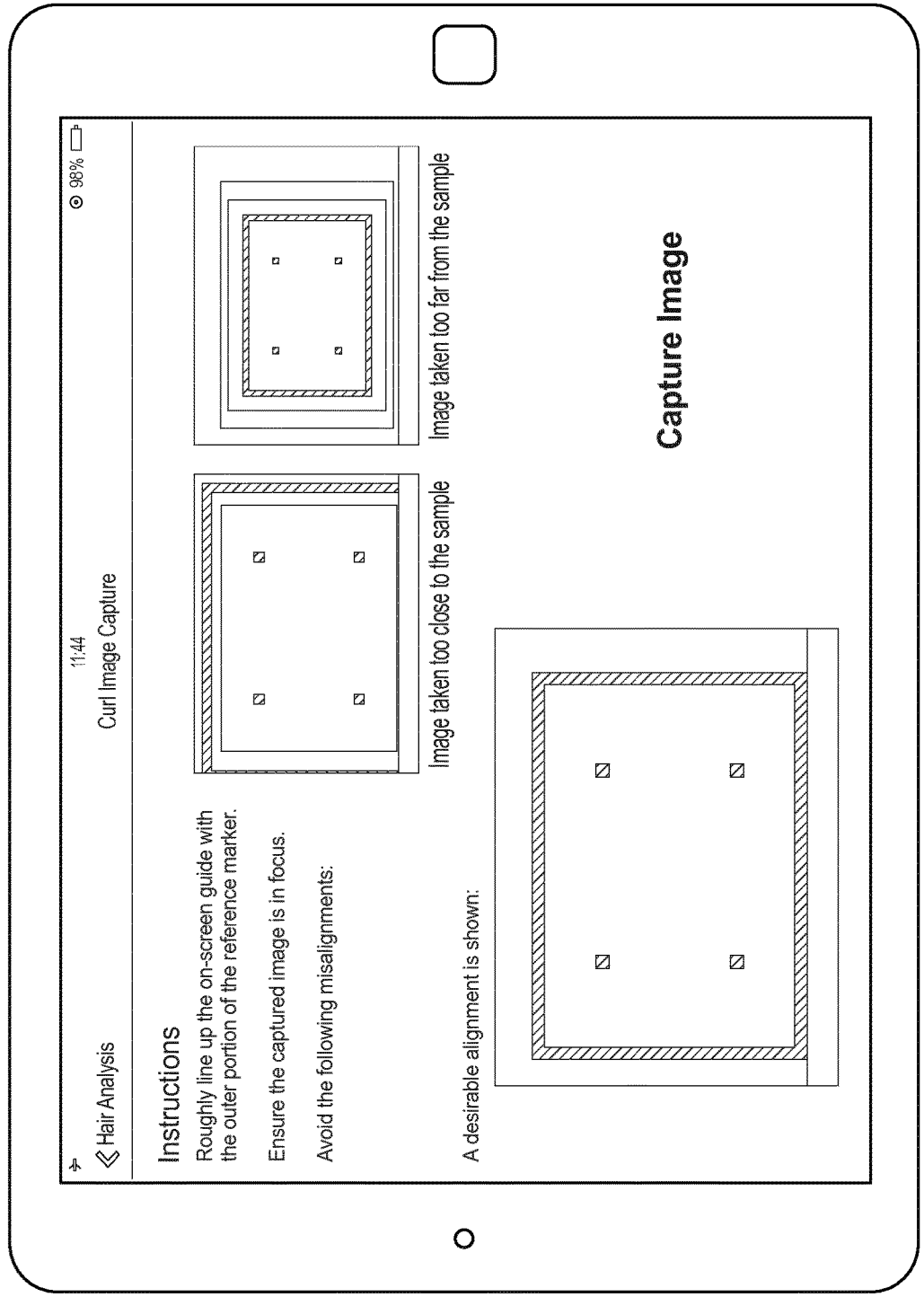
FIG. 11 shows an instruction display on the mobile device.

FIG. 11 shows an instruction display on the mobile device 20; the instruction display providing the user with instructions of the steps required to carry out the step of acquiring the first image. The instruction page contains a link that the user can click on to proceed to the image capture when they are ready.

Figure 12:
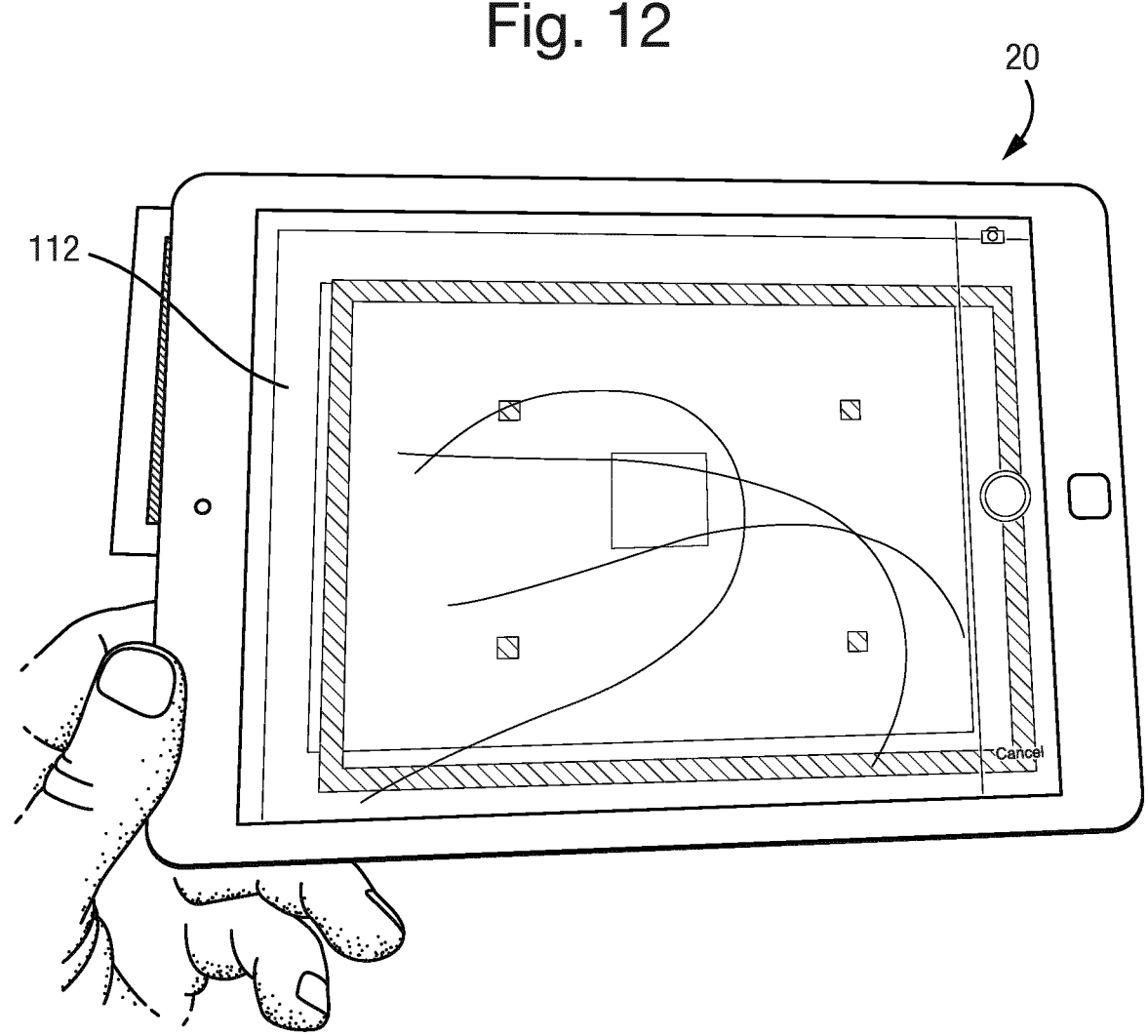
FIG. 12 shows an example of obtaining a first image of the hairs and reference card of FIGS. 10 and 11.

The capture of the first image at a first distance can be seen in FIG. 12. The screen of the mobile device exhibits the optical input received by the digital imaging device (i.e. the camera) of the mobile device. As can be seen from FIG. 12, the computer program (application) running on the mobile device provides an overlay 112 on top of the live feed; the overlay having the same relative dimensions as the first reference marker. The user aligns the inner edge of the overlay boarder with the outer edge of the first reference marker as viewed through the screen before recording the image by pressing a capture button on the screen.

Figure 13:
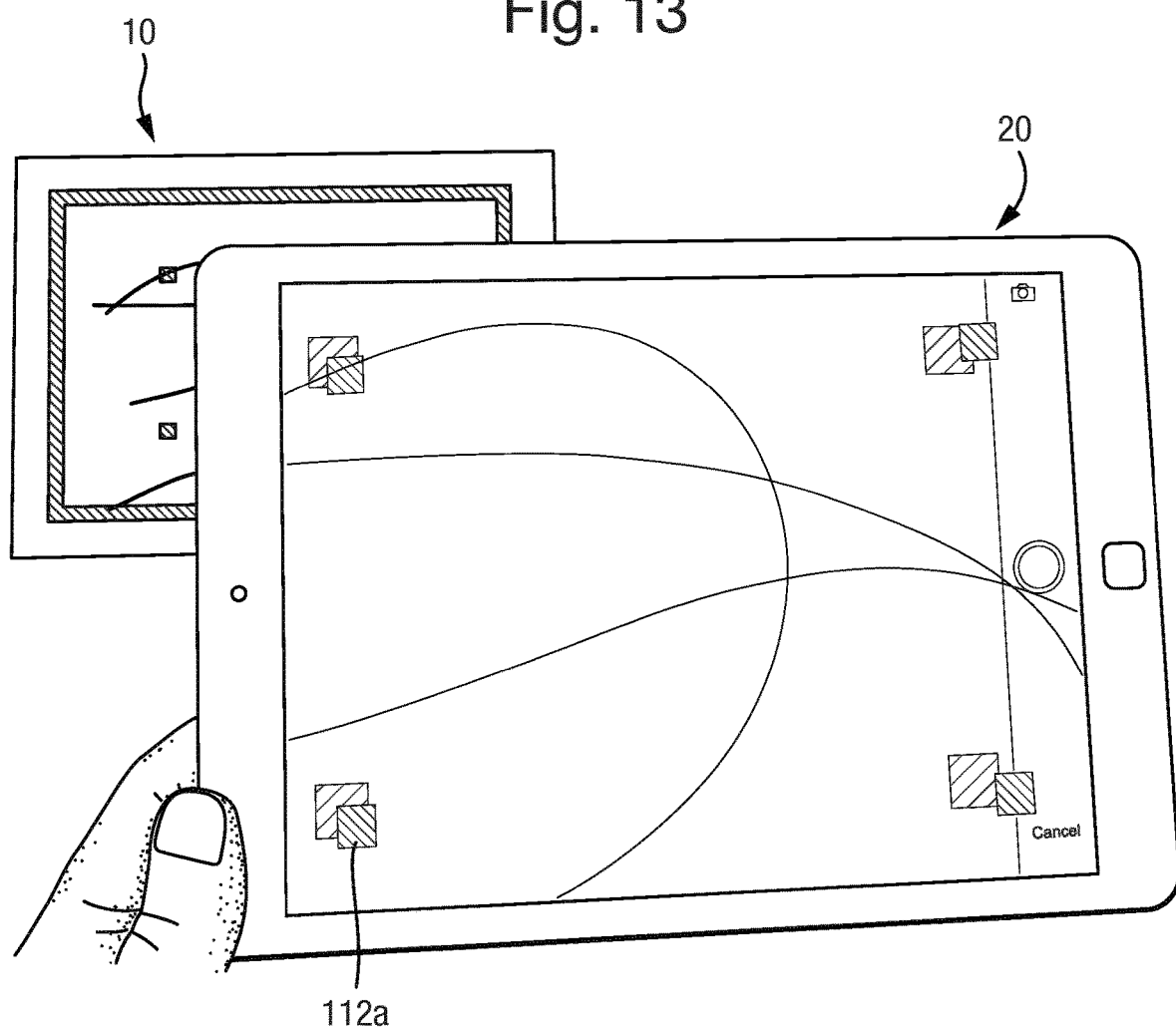
FIG. 13 shows an example of obtaining a second image of the hairs and the reference card of FIGS. 10 to 12.

FIG. 13 shows the capture of the second image at a second distance. The screen of the mobile device exhibits the optical input received by the digital imaging device (i.e. the camera) of the mobile device. As can be seen from FIG. 13, the computer program (application) running on the mobile device provides a second overlay 112a on top of the live feed; the second overlay having the same relative shape and dimensions as the second reference marker. The user aligns the inner edge of the overlay boarder with the outer edge of the first reference marker as viewed through the screen before recording the image by pressing a capture button on the screen.

Figure 14:
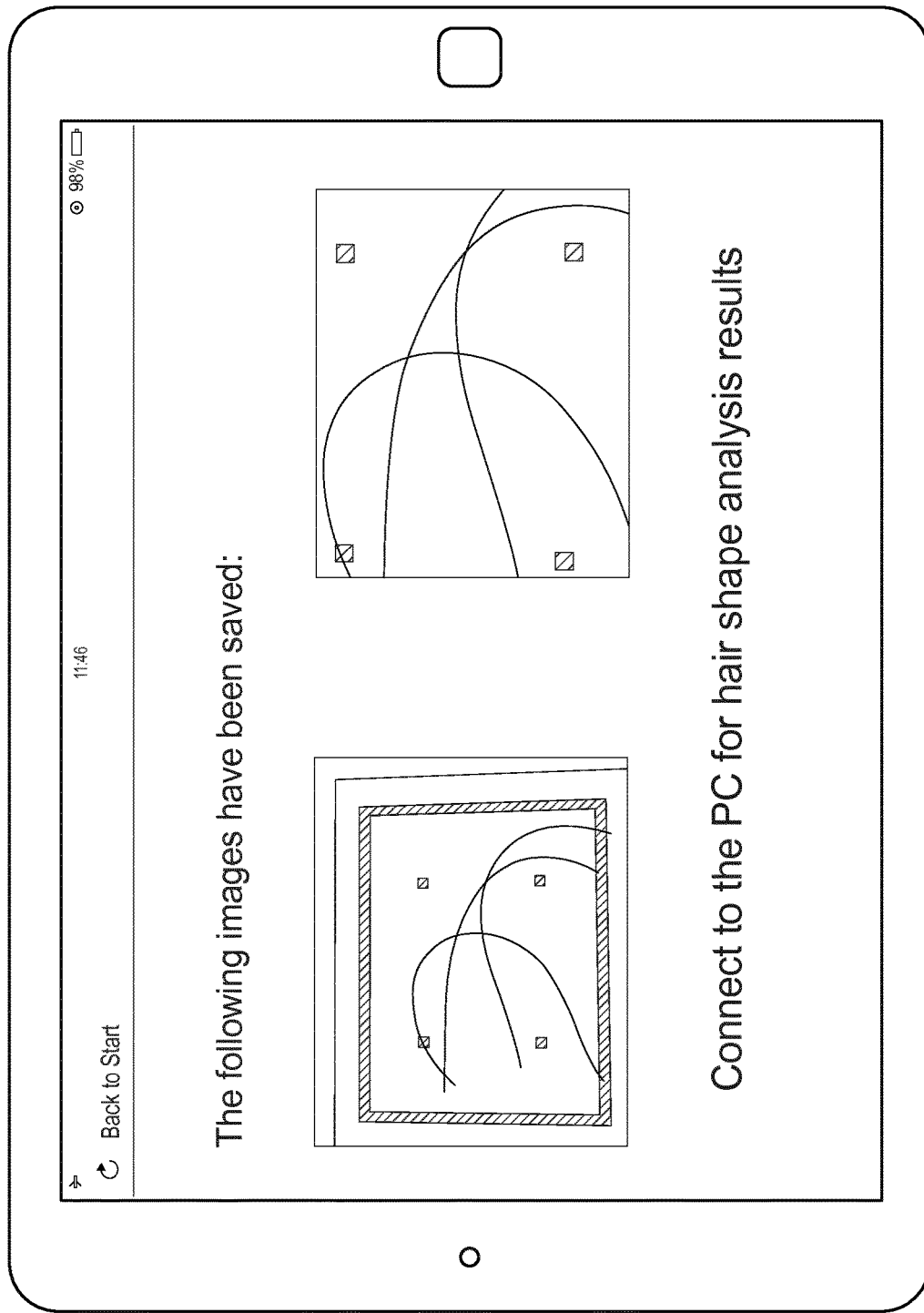
FIG. 14 shows an example of a further instruction screen.

FIG. 14 shows a further user instruction screen; this time confirming that the images have been taken, displaying the images, and instructing the user to connect the mobile device to an external computer for analysis. A direct connection is shown as a dotted line in FIG. 3. Alternatively, connection to the external computer 30 could be achieved via a network 40.

Figure 15:
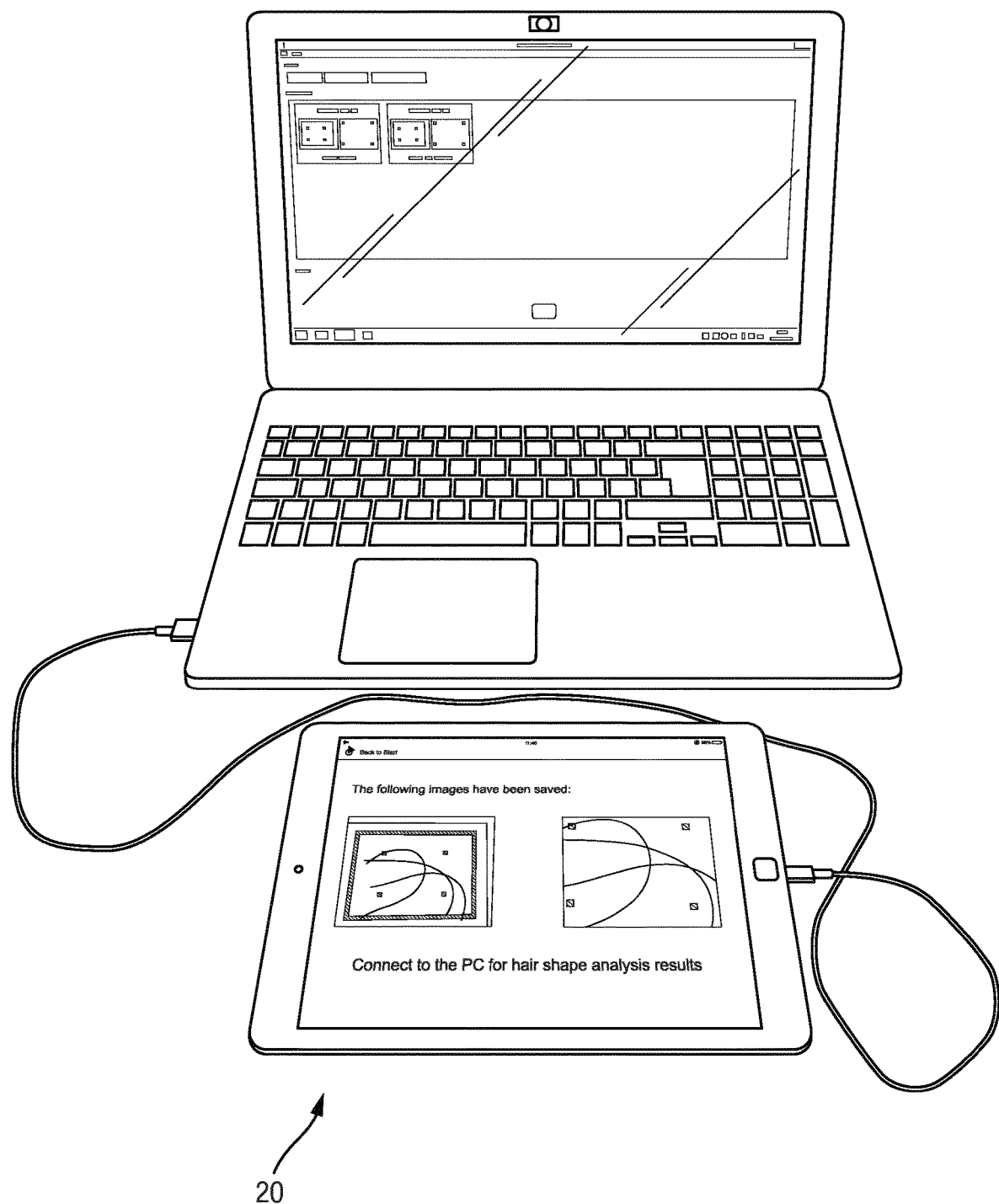
FIG. 15 shows an example of one way of transferring data from the mobile device to a computer module in an external computer.

FIG. 15 shows an example of one way of transferring data from the mobile device to a computer module in an external computer directly via a cable. It is envisages that large external servers could be used instead of personal computers and that these could be contacted via a network 40 such as a LAN or WAN.

Figure 16:
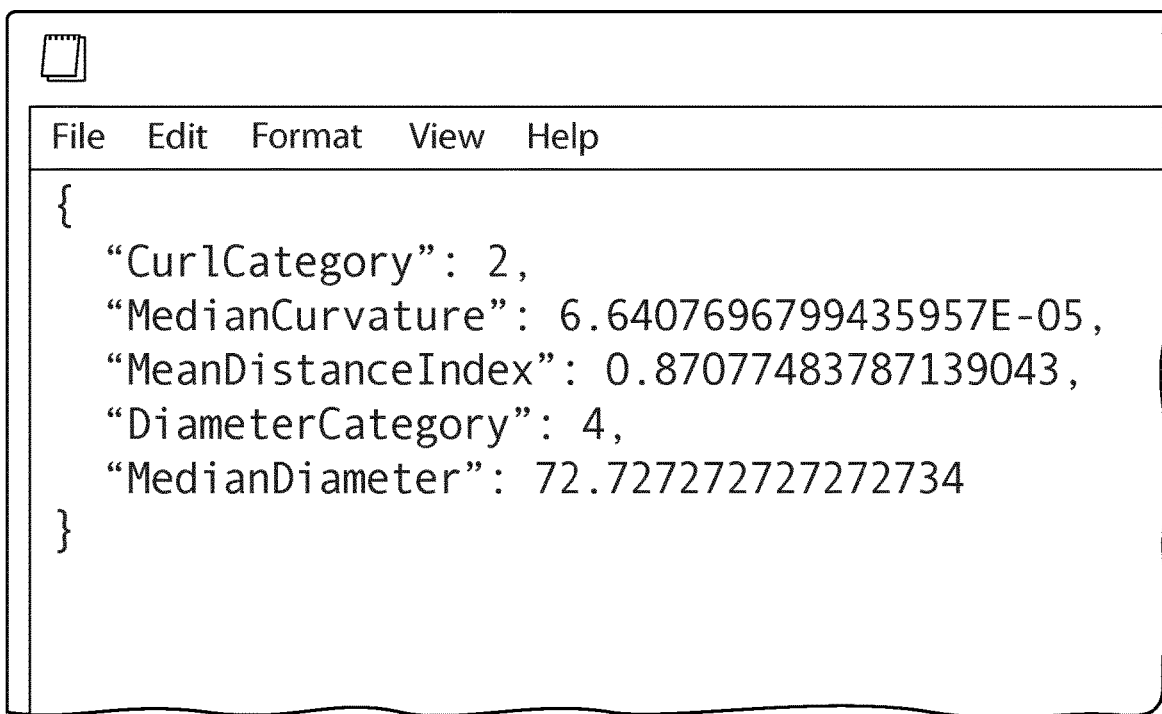
FIG. 16 shows an example of an output of extracted measurements.
Figure 25:
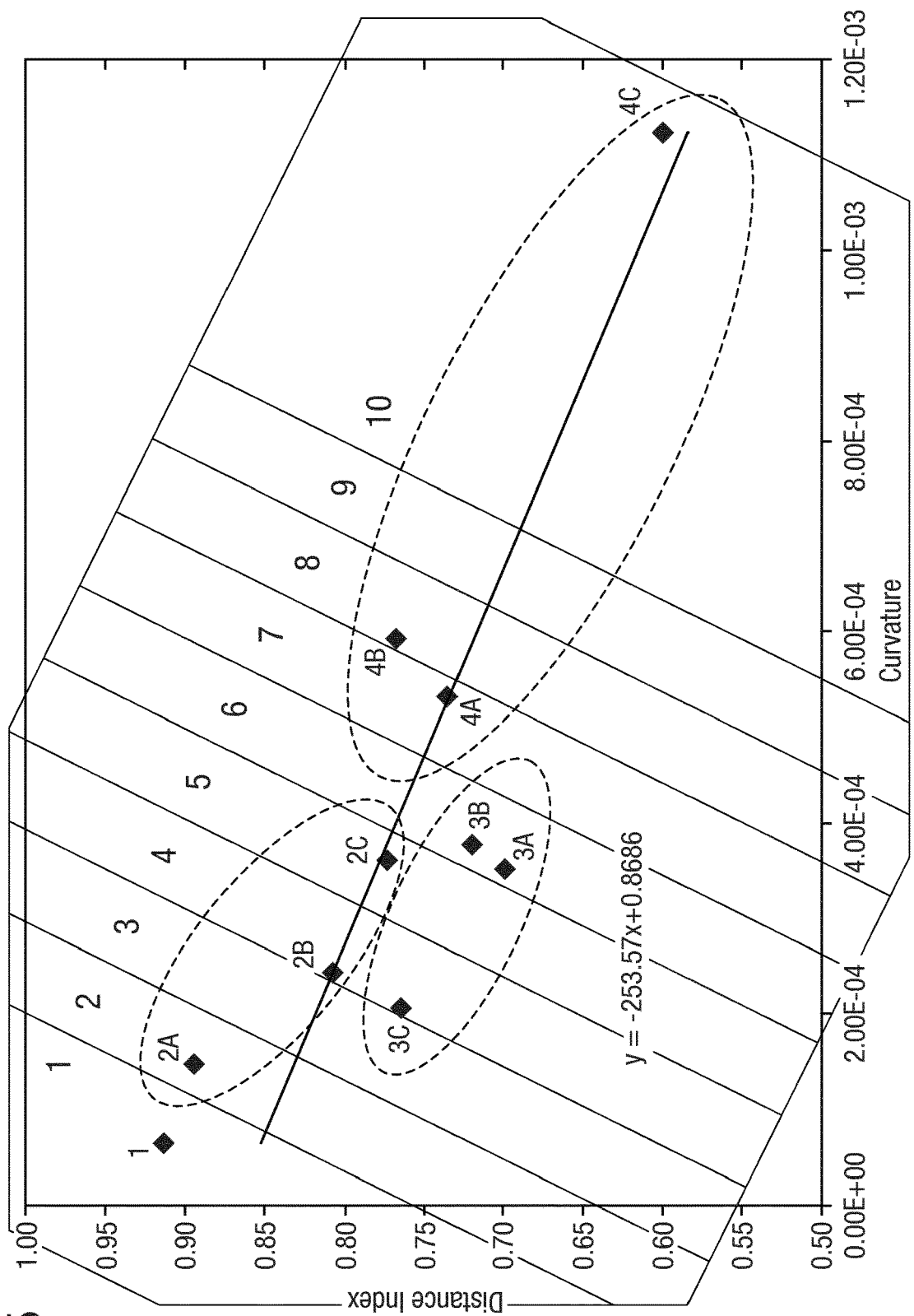
FIG. 25 shows the curl measurements of FIG. 24 with curl categories applied.

FIG. 16 shows an example of an output of extracted measurements which includes a curl category, median curvature, mean distance index, diameter category and median diameter. Curl category and diameter category are assigned based on the actual measured values. Examples of the curl category and the way in which they are assigned is shown in FIG. 25. These are chosen to provide an easy to reference numerical value for curl type. Examples of diameter category are shown in FIG. 27.

Figure 17:
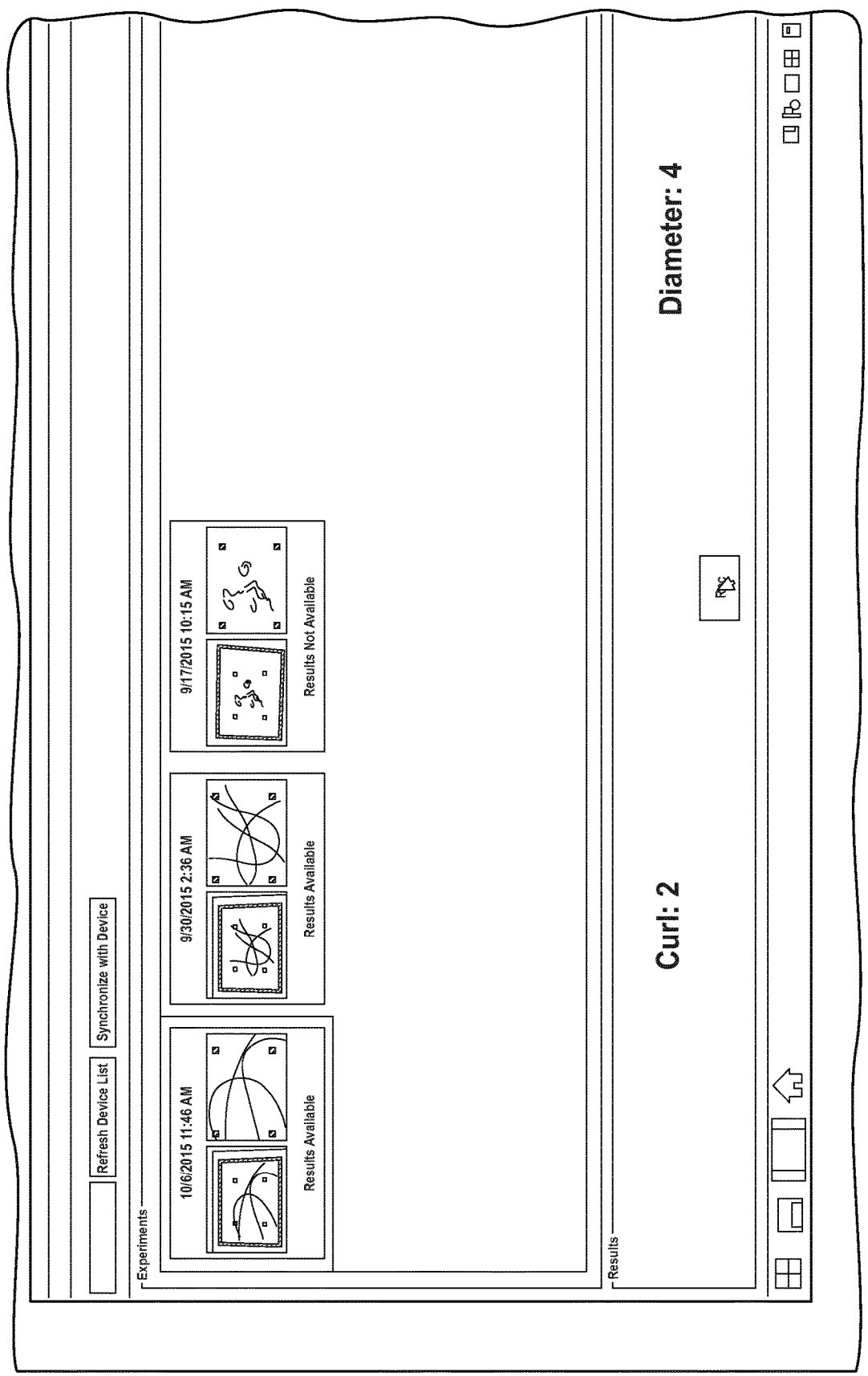
FIG. 17 shows an example of shows an example of extracted results stored by an external computer.

Extracted results can be stored in the external computer for future reference as shown in FIG. 17.

Figure 18:
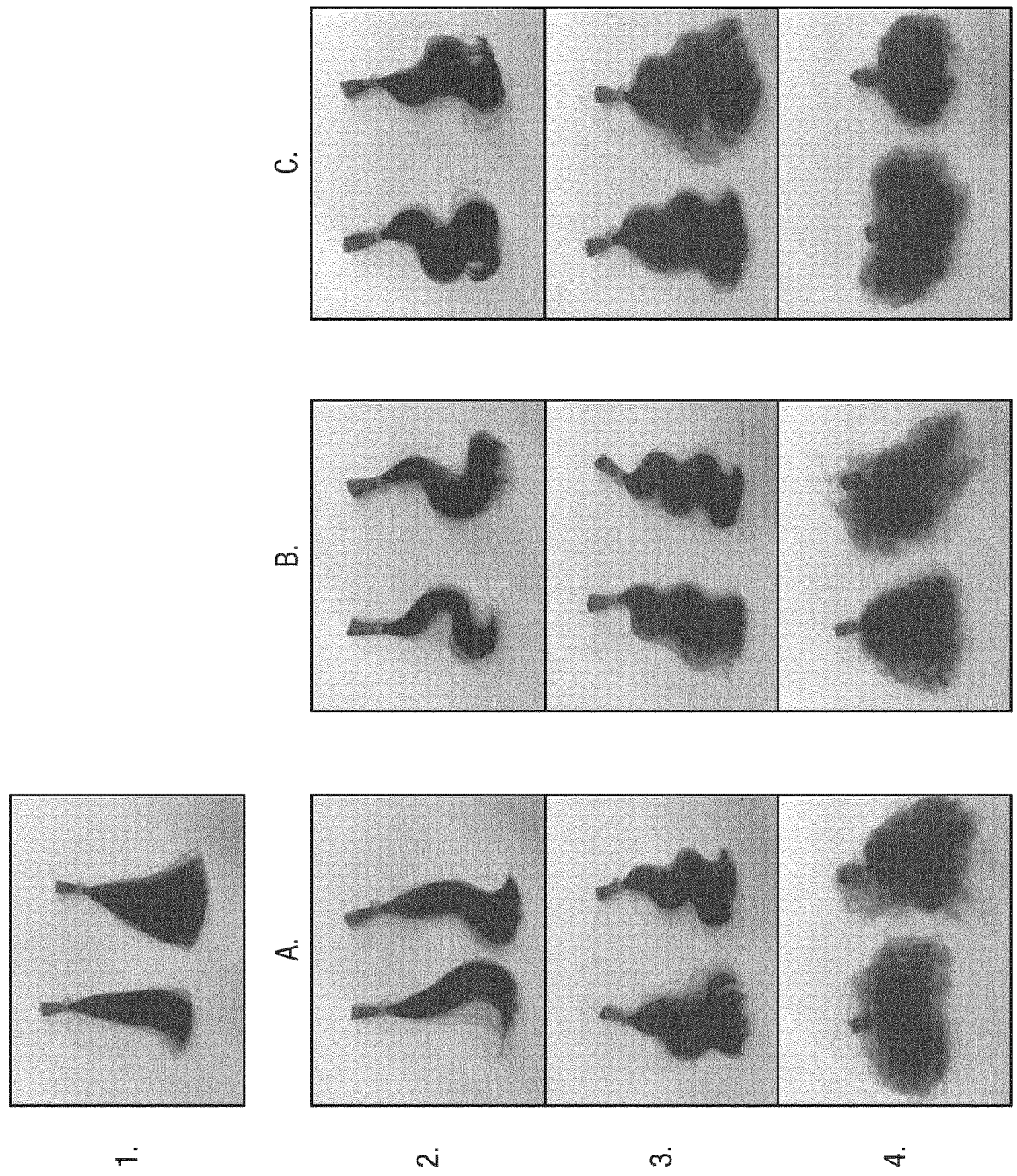
FIG. 18 shows an example of switches of hair grouped according to curl.
Figure 19:
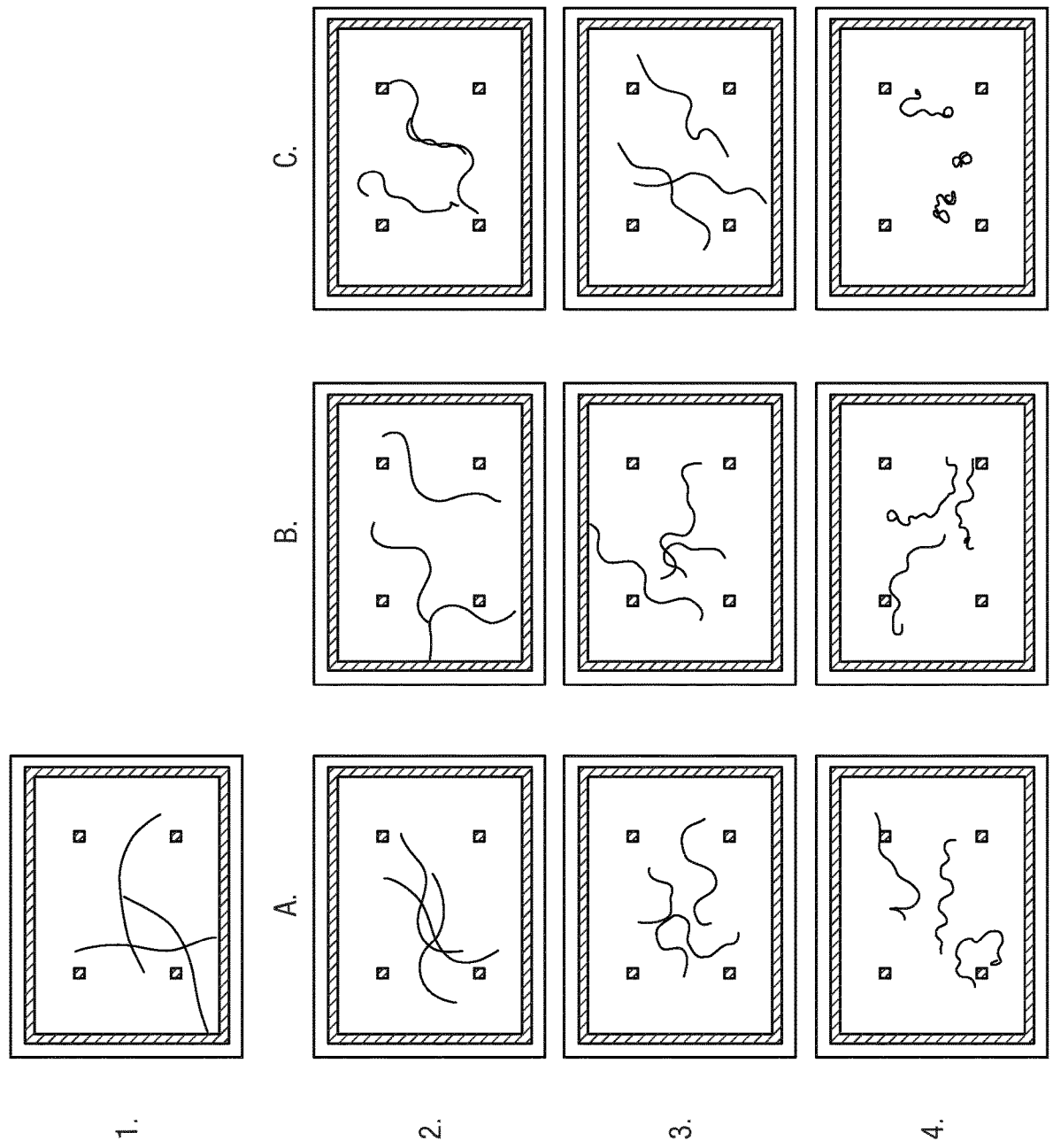
FIG. 19 shows three hairs from each group of FIG. 18 placed on the reference card of FIG. 1.
Figure 20:
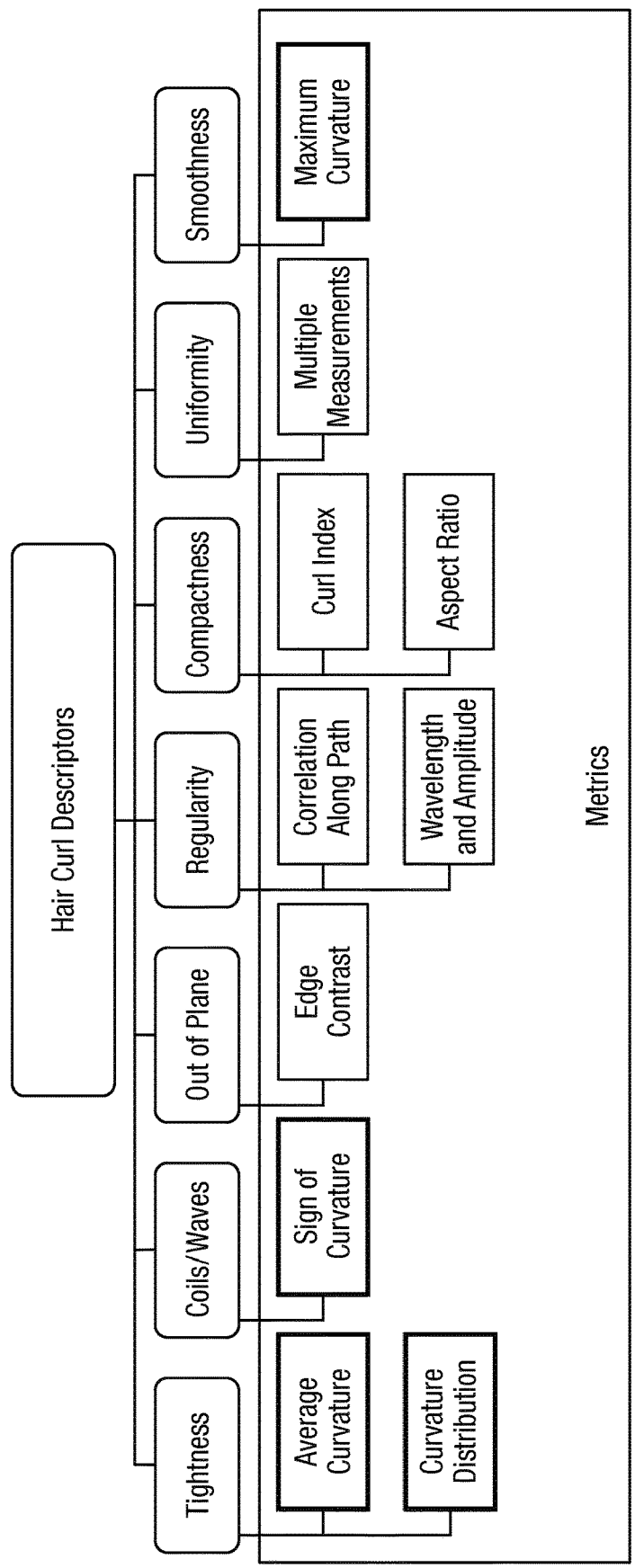
FIG. 20 provides an overview of hair curl descriptions.
Figure 21A:
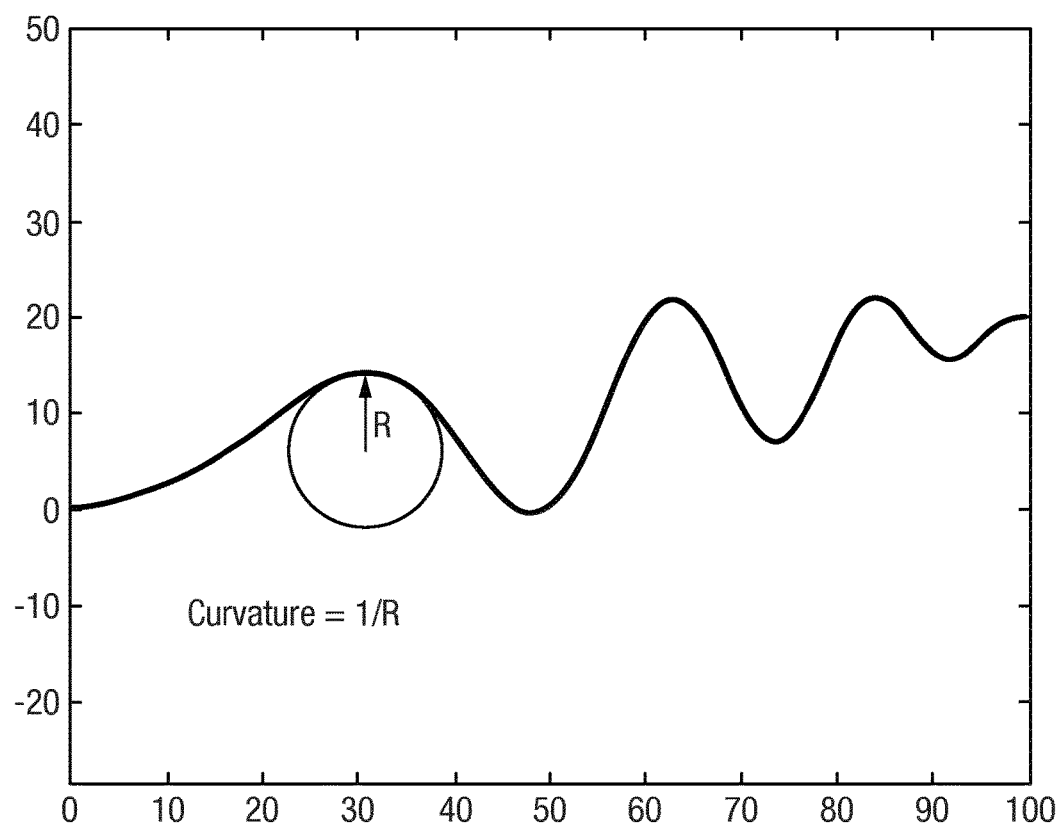
FIG. 21 depicts examples of measurements of some characteristics of curl.
Figure 21B:
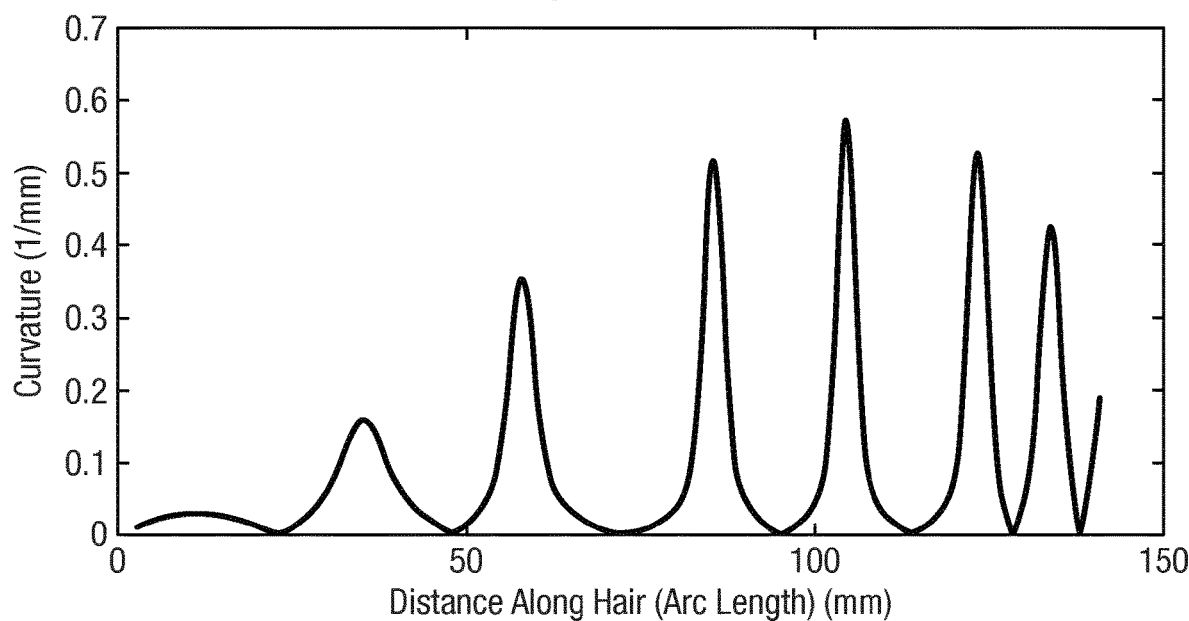

FIG. 18 shows an example of switches of hair grouped according to curl. The relationship between these bought switches and the resulting assigned curl category is shown in FIG. 25. FIG. 19 shows three hairs from each group of FIG. 18 placed on the reference card of FIG. 1;

FIG. 20 provides an overview of hair curl descriptions. Average curvature, curvature distribution, sign of curvature and maximum curvature can all be understood in relation to FIGS. 21A and 21B.

Figure 23:
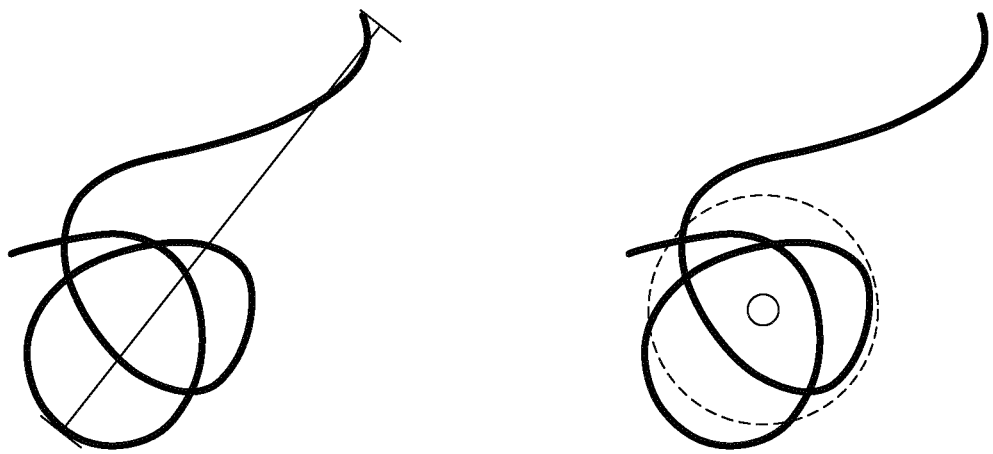
FIG. 23 depicts the examples of measurements of some characteristics of curl as shown in FIG. 22, but for hair with a different curl.

Curl index (and also mean distance index) can be understood in relation to FIGS. 22 and 23. These drawings also indirectly demonstrate the advantages of acquiring two images, from a first and second distance. The image on the right of each of FIG. 22 and FIG. 23 includes a dotted circle delineating a central area. In this dotted circle, it may appear that there are two separate hairs. However, if another image which is more zoomed-out is also used, such as that on the left of each of FIGS. 22 and 23, then it is clear that this is in fact one curly hair crossing itself numerous times. So, with this knowledge (i.e. from the first image), it is then possible ensure that superfluous diameter measurements are not made.

Figure 24:
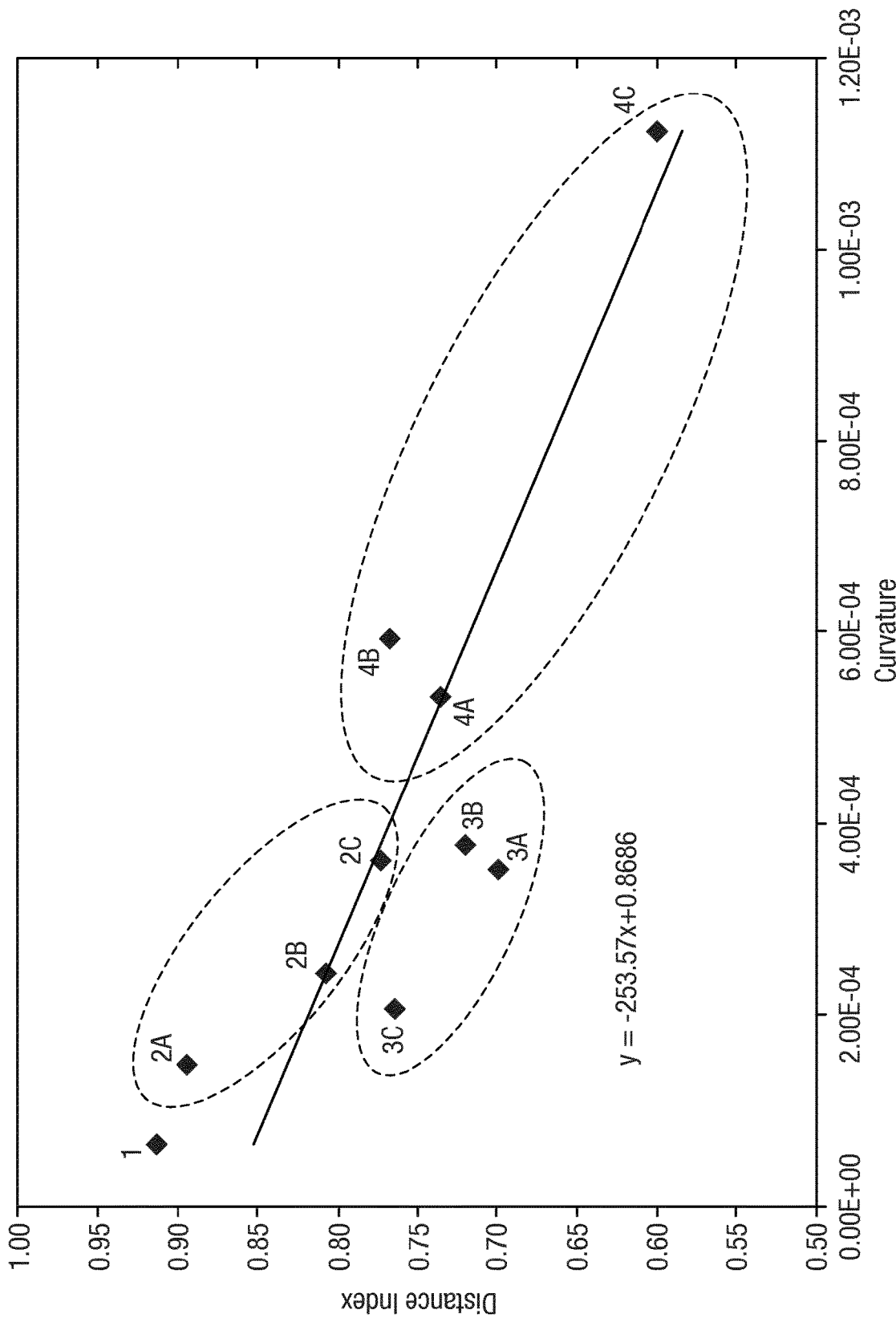
FIG. 24 shows curl measurement results for each of the hair types shown in FIGS. 18 and 19.

FIG. 24 shows curl measurement results for each of the hair types shown in FIGS. 18 and 19 where measured distance index is plotted against measured curvature. FIG. 25 shows the same curl measurements of FIG. 23 with curl categories 1 to 10 applied, 1 being the straightest and 10 being the curliest.

Figure 26:
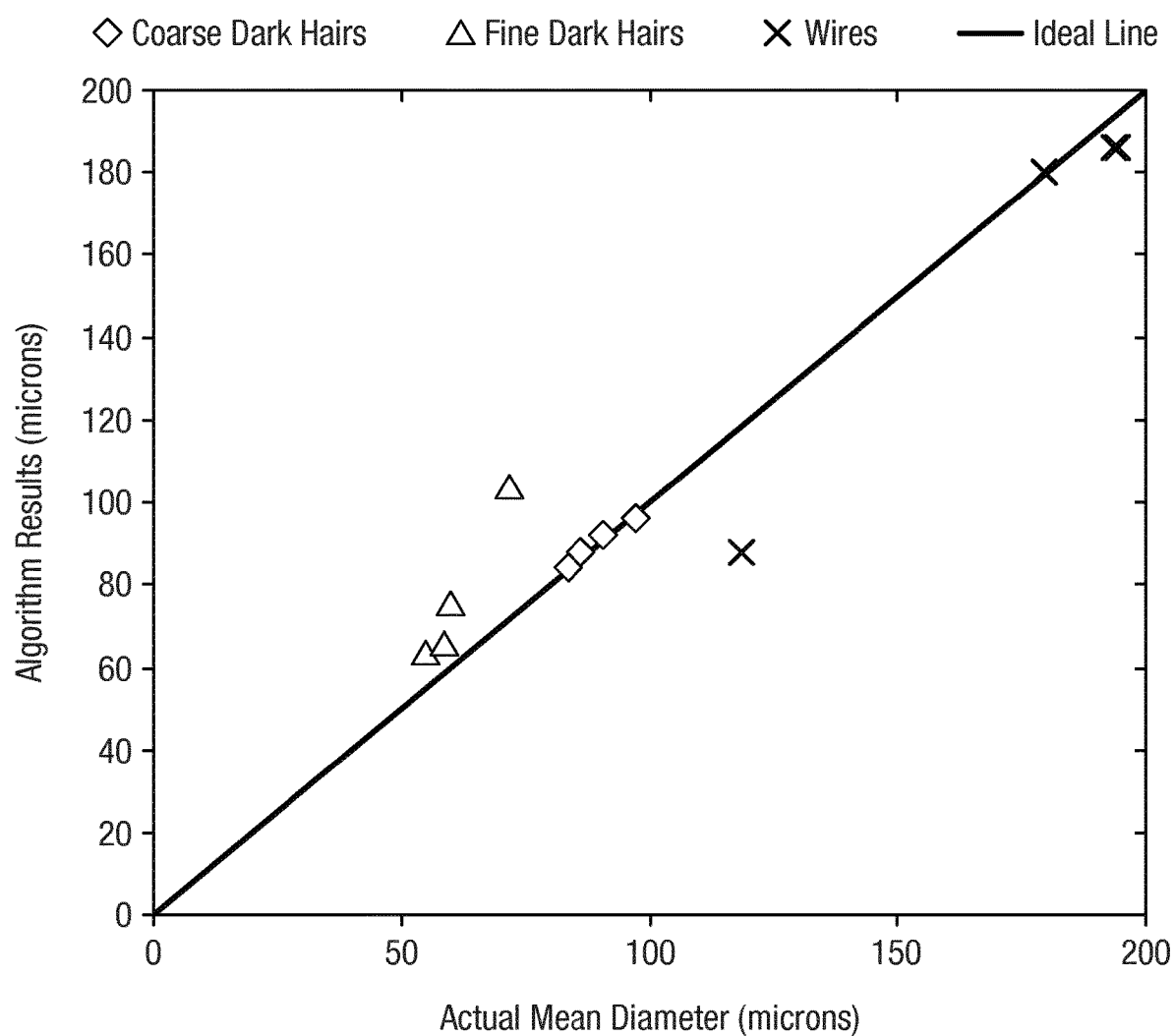
FIG. 26 shows an example of diameter measurement results.

FIG. 26 shows an example of diameter measurement results for a sample of hairs of different thicknesses. The algorithm measured diameters are plotted against the actual measurements (LSM mean diameter). It was found that the type of mobile device used affected the accuracy of the results. Results taken using a tablet showed a good correlation, but mapping between measured diameters is not as close to 1:1 as for a mobile phone. This is likely to be due to the camera quality, and may require device specific correction factors. Diameter measurements are therefore highly dependent on device camera performance.

FIG. 27 gives an example of diameter ranges for characterisation.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

The invention claimed is:

1. A method of measuring indications of a hair type of a user, the method comprising:
   providing a mobile device;
   providing a reference card, the reference card including a first reference marker defining a first image area and a second reference marker defining a second image area, the first image area comprising the second image area;
   providing a hair at a surface of the reference card and within the second image area;
   acquiring a first image of the hair using the mobile device;
   identifying a path of the hair along the reference card; and
   calculating a diameter of the hair from the first image.

2. The method of claim 1, further comprising calculating a curve of the hair from the identified path.

3. The method of claim 1, wherein acquiring the first image includes:
   providing a real time view of an input of a digital imaging device on the mobile device;
   providing an overlay on top of the real time view, the overlay having the same shape as the first reference marker.

4. The method of claim 1, further comprising acquiring a second image;
   wherein the first image is acquired at a first distance from the reference card; and
   wherein the second image is acquired at a second distance from the reference card, the second distance being different from the first distance.

5. The method of claim 1, wherein identifying the path of the hair along the reference card comprises:
   applying an edge detection algorithm to the first image;
   identifying a center line of the hair at a plurality of points along the hair; and
   applying a fit to the plurality of points.

6. The method of claim 1, wherein calculating the diameter of the hair from the first image includes:
   measuring an orientation of a given point on the identified path; and
   taking a cross section perpendicular to the orientation of the path.

7. The method of claim 6, wherein taking the cross section perpendicular to the orientation of the path includes:
   taking an intensity profile along a direction perpendicular to the orientation of the path;
   locating two peaks on the intensity profile, the two peaks corresponding to two opposite edges of the hair; and
   determining a maximum distance between the two peaks, the maximum distance corresponding to the diameter of the hair.

8. A system for measuring a hair type of a user, the system comprising:
   a reference card, the reference card including a reference marker; and
   a mobile device, the mobile device configured to:
      provide on a screen of the mobile device an overlay configured to be aligned with the reference marker;
      acquire a first image while the overlay is aligned with the reference marker, the first image comprising the reference marker and a hair;
      acquire a second image of at least a portion of the hair;
      identify a path of the hair along the reference card; and
      calculate a diameter of the hair from the identified path.

9. The system of claim 8, wherein the mobile device is further configured to calculate a curve of the hair from the identified path.

10. The system of claim 8, wherein the reference marker is a first reference marker, the reference card further comprising:
    a second reference marker for aligning the mobile device with the reference card when obtaining the second image using the mobile device.

11. The system of claim 10, wherein the first reference marker defines a first image area and the second reference marker defines a second image area, the second image area located within the first image area.

12. A non-transitory computer readable media having computer-executable instructions embodied therein that, when executed by a processor of a mobile device, cause the mobile device to perform operations for measuring indications of a hair type of a user, the operations comprising:
    acquiring an image of a hair using the mobile device;
    identifying a path of the hair; and
    calculating a diameter of the hair from the path by:
       intersecting the path with a perpendicular line;
       calculating an intensity profile of the perpendicular line;
       locating two peaks on the intensity profile; and
       calculating a distance between the two peaks, the distance being equal to the diameter of the hair.

13. The computer readable media of claim 12, wherein acquiring the image includes:
    providing a real time view of an input of a digital imaging device on the mobile device; and
    providing an overlay on top of the real time view, the overlay having the same shape as a reference marker in the real time view.

14. The computer readable media of claim 12, further comprising calculating a curve of the hair from the path.

15. The computer readable media of claim 12, wherein identifying the path of the hair further comprises:
    detecting a first edge and a second edge of the hair within the image;
    identifying a center point positioned halfway between the first edge and the second edge at a point where the first edge and the second edge are parallel to each other; and
    identifying the path as being a line that intersects the center point.

16. The computer readable media of claim 12, wherein the path is fit to a polynomial of a single indeterminate.

17. A method of measuring indications of a hair type of a user, the method comprising the steps of:
    providing a mobile device;
    providing a reference card, the reference card including a first reference marker;
    providing a hair at a surface of the reference card;
    obtaining a first image of the hair on the reference card, the first image acquired at a first distance from the reference card;
    obtaining a second image of the hair on the reference card, the second image acquired at a second distance from the reference card, the second distance being less than the first distance;
    identifying a path of the hair along the reference card; and
    calculating a diameter of the hair from the first image and the second image.

18. The method of claim 17, wherein:
    the reference card further comprises a second reference marker for aligning the mobile device with the reference card when obtaining the second image; and
    the first reference marker is for aligning the mobile device with the reference card when obtaining the first image.

19. The method of claim 17, wherein the path is fit to a polynomial.

20. A method of measuring indications of a hair type of a user, the method comprising:
- providing a mobile device;
- providing a reference card, the reference card including a reference marker;
- providing a hair at a surface of the reference card;
- acquiring an image of the hair using the mobile device;
- identifying a path of the hair along the reference card; and
- calculating a diameter of the hair from the image, comprising:
  - measure an orientation of a given point on the identified path;
  - take an intensity profile along a direction perpendicular to the orientation of the path;
  - locate two peaks on the intensity profile, the two peaks corresponding to two opposite edges of the hair; and
  - measure the diameter of the hair at the given point as a distance between the two peaks.

* * * * *